(12) United States Patent
Leonard et al.

(10) Patent No.: US 9,089,484 B2
(45) Date of Patent: *Jul. 28, 2015

(54) PHARMACEUTICAL COMPOSITIONS OF SELECTIVE FACTOR XA INHIBITORS FOR ORAL ADMINISTRATION

(75) Inventors: Thomas W. Leonard, Wilmington, NC (US); David C. Coughlan, Kildare (IE); Alan Cullen, Dublin (IE)

(73) Assignee: Merrion Research III Limited, Dublin (IE)

(*) Notice: Subject to any disclaimer, the term of this patent is extended or adjusted under 35 U.S.C. 154(b) by 473 days.

This patent is subject to a terminal disclaimer.

(21) Appl. No.: 13/073,202

(22) Filed: Mar. 28, 2011

(65) Prior Publication Data

US 2011/0236474 A1    Sep. 29, 2011

Related U.S. Application Data

(60) Provisional application No. 61/317,961, filed on Mar. 26, 2010, provisional application No. 61/423,261, filed on Dec. 15, 2010.

(51) Int. Cl.

| *A61K 8/21* | (2006.01) |
|---|---|
| *A61K 8/30* | (2006.01) |
| *A61Q 11/00* | (2006.01) |
| *A61K 9/107* | (2006.01) |
| *A61K 9/00* | (2006.01) |
| *A61K 31/715* | (2006.01) |
| *A61K 31/727* | (2006.01) |
| *A61K 47/12* | (2006.01) |

(52) U.S. Cl.
CPC ............... *A61K 9/1075* (2013.01); *A61K 9/009* (2013.01); *A61K 31/715* (2013.01); *A61K 31/727* (2013.01); *A61K 47/12* (2013.01)
USPC .......................................................... 424/452

(58) Field of Classification Search
None
See application file for complete search history.

(56) References Cited

U.S. PATENT DOCUMENTS

| 4,525,339 A | 6/1985 | Behl et al. |
|---|---|---|
| 4,590,062 A | 5/1986 | Jang |
| 4,654,155 A | 3/1987 | Kipp et al. |
| 4,656,161 A | 4/1987 | Herr |
| 4,764,375 A | 8/1988 | Paradissis |
| 4,786,508 A | 11/1988 | Ghebre-Sellassie et al. |
| 4,789,547 A | 12/1988 | Song et al. |
| 4,900,730 A | 2/1990 | Miyauchi |
| 4,996,058 A | 2/1991 | Sinnreich |
| 5,110,606 A | 5/1992 | Geyer et al. |
| 5,169,933 A | 12/1992 | Anderson et al. |
| 5,190,748 A | 3/1993 | Bachynsky et al. |
| 5,221,734 A | 6/1993 | Burk et al. |
| 5,229,130 A | 7/1993 | Sharma et al. |
| 5,288,497 A | 2/1994 | Stanley et al. |
| 5,346,701 A | 9/1994 | Heiber et al. |
| 5,444,041 A | 8/1995 | Owen et al. |
| 5,506,207 A | 4/1996 | Rivier et al. |
| 5,541,155 A | 7/1996 | Leone-Bay et al. |
| 5,631,347 A | 5/1997 | Baker et al. |
| 5,633,226 A | 5/1997 | Owen et al. |
| 5,639,469 A | 6/1997 | Benes et al. |
| 5,646,109 A | 7/1997 | Owen et al. |
| 5,650,386 A | 7/1997 | Leone-Bay et al. |
| 5,688,761 A | 11/1997 | Owen et al. |
| 5,707,648 A | 1/1998 | Yiv |
| 5,714,477 A | 2/1998 | Einarsson |
| 5,736,161 A | 4/1998 | Garces et al. |
| 5,807,983 A | 9/1998 | Jiang et al. |
| 5,821,222 A | 10/1998 | Bonse et al. |
| 5,821,230 A | 10/1998 | Jiang et al. |
| 5,840,685 A | 11/1998 | Fujii et al. |
| 5,854,281 A | 12/1998 | Uekama et al. |
| 5,863,555 A | 1/1999 | Heiber et al. |
| 5,912,009 A | 6/1999 | Venkateshwaran et al. |
| 5,952,000 A | 9/1999 | Venkateshwaran et al. |
| 5,977,175 A | 11/1999 | Lin |
| 5,998,432 A | 12/1999 | Walsh et al. |
| 6,001,390 A | 12/1999 | Yum et al. |
| 6,004,984 A | 12/1999 | Goulet et al. |

(Continued)

FOREIGN PATENT DOCUMENTS

| CN | 1243667 A | 2/2000 |
|---|---|---|
| CN | 1606432 A | 4/2005 |

(Continued)

OTHER PUBLICATIONS

Choay et al. (Structure-activity relationship in heparin: a synthetic pentasaccharide with high affinity for antithrombin 1983.*
Breddin ("The role of antithrombin agents and factor Xa inhibitors in antithrombotic treatment").*
Allen, "Ansel's Pharmaceutical Dosage Forms and Drug Delivery Systems," 8th Ed., Lippincott Williams & Wilkins, 51-58 (2005).
Anderberg et al., "Sodium Caprate Effects Dilations in Human Intestinal Tight Junctions and Enhances Drug Absorption by the Paracellular Route," Pharm. Res. 10(6):857-864 (1993).
Andriuoli et al., "Heparin by Alternative Routes of Administration", Haemostasis 20:(suppl 1):154-158 (1990).
Appendix A: Webpage publication provided by Lambent Technologies www.petroferm.com/prodinfo.asp?bus=2&mkt=4&app=3.

(Continued)

*Primary Examiner* — Snigdha Maewall
(74) *Attorney, Agent, or Firm* — Myers Bigel Sibley & Sajovec, P.A.

(57) ABSTRACT

The present invention provides pharmaceutical compositions for oral administration comprising a therapeutically effective amount of a selective factor Xa inhibitor or a pharmaceutically acceptable salt thereof and an enhancer, wherein the enhancer is a medium chain fatty acid or a salt, ester, ether, or derivative of a medium chain fatty acid and has a carbon chain length of from about 4 to about 20 carbon atoms. The present invention also provides a method for obtaining a reproducible bioavailability of selective factor Xa inhibitor in an object after oral administration comprising orally administering a pharmaceutical composition as described above.

27 Claims, 2 Drawing Sheets

(56) References Cited

U.S. PATENT DOCUMENTS

| | | |
|---|---|---|
| 6,015,801 A | 1/2000 | Daifotis et al. |
| 6,017,559 A | 1/2000 | Mulqueen et al. |
| 6,017,944 A | 1/2000 | Chu et al. |
| 6,025,366 A | 2/2000 | Walsh et al. |
| 6,068,850 A | 5/2000 | Stevenson et al. |
| 6,077,847 A | 6/2000 | Walsh et al. |
| 6,077,858 A | 6/2000 | Goulet et al. |
| 6,124,261 A | 9/2000 | Stevenson et al. |
| 6,147,088 A | 11/2000 | Goulet et al. |
| 6,150,352 A | 11/2000 | Goulet et al. |
| 6,150,522 A | 11/2000 | Goulet et al. |
| 6,156,767 A | 12/2000 | Goulet et al. |
| 6,156,772 A | 12/2000 | Goulet et al. |
| 6,200,602 B1 | 3/2001 | Watts et al. |
| 6,214,798 B1 | 4/2001 | Semple et al. |
| 6,235,712 B1 | 5/2001 | Stevenson et al. |
| 6,248,363 B1 | 6/2001 | Patel et al. |
| 6,270,804 B1 | 8/2001 | Getz et al. |
| 6,296,881 B1 | 10/2001 | Hata et al. |
| 6,326,360 B1 | 12/2001 | Kanazawa et al. |
| 6,372,728 B1 | 4/2002 | Ungell |
| 6,379,960 B1 | 4/2002 | Popoff et al. |
| 6,468,559 B1 | 10/2002 | Chen et al. |
| 6,524,557 B1 | 2/2003 | Backstrom et al. |
| 6,638,530 B1 | 10/2003 | Ishibashi et al. |
| 6,747,014 B2 | 6/2004 | Teng et al. |
| 6,747,125 B1 | 6/2004 | Hoeger et al. |
| 6,875,843 B2 | 4/2005 | Jacobson |
| 6,949,258 B2 | 9/2005 | Zhang |
| 7,098,305 B2 | 8/2006 | Deghenghi et al. |
| 7,154,002 B1 | 12/2006 | Bressi et al. |
| 7,214,662 B2 | 5/2007 | Sarlikiotis et al. |
| 7,410,957 B2 | 8/2008 | Bauss et al. |
| 7,605,123 B2 | 10/2009 | Radhakrishnan et al. |
| 7,658,938 B2 | 2/2010 | Cumming et al. |
| 7,670,626 B2 | 3/2010 | Clancy et al. |
| 7,704,977 B2 | 4/2010 | Leonard |
| 8,053,429 B2 | 11/2011 | Cumming et al. |
| 8,119,159 B2 | 2/2012 | Cumming et al. |
| 8,323,689 B2 | 12/2012 | Cumming et al. |
| 8,323,690 B2 | 12/2012 | Cumming et al. |
| 8,828,431 B2 | 9/2014 | Cumming et al. |
| 8,999,383 B2 | 4/2015 | Lee et al. |
| 2002/0002140 A1 | 1/2002 | Holick et al. |
| 2003/0031757 A1 | 2/2003 | Akashe et al. |
| 2003/0091623 A1 | 5/2003 | Cumming et al. |
| 2003/0100509 A1 | 5/2003 | Sarlikiotis et al. |
| 2003/0114525 A1 | 6/2003 | Kammer et al. |
| 2003/0139378 A1 | 7/2003 | Daifotis et al. |
| 2003/0166508 A1 | 9/2003 | Zhang |
| 2003/0176397 A1 | 9/2003 | Lichtenberger |
| 2003/0181421 A1 | 9/2003 | Horowitz et al. |
| 2004/0087631 A1 | 5/2004 | Bacopoulos et al. |
| 2004/0147484 A1 | 7/2004 | Boyd et al. |
| 2004/0157799 A1 | 8/2004 | Seaman et al. |
| 2005/0065117 A1 | 3/2005 | Lee |
| 2005/0080075 A1 | 4/2005 | Nichols et al. |
| 2005/0119331 A1 | 6/2005 | Butler et al. |
| 2005/0157799 A1 | 7/2005 | Raman |
| 2005/0163849 A1 | 7/2005 | Wong et al. |
| 2005/0221501 A1 | 10/2005 | Arnot et al. |
| 2005/0232981 A1 | 10/2005 | Ben-Sasson |
| 2005/0260262 A1 | 11/2005 | Dansereau et al. |
| 2006/0018874 A1 | 1/2006 | Radhakrishnan et al. |
| 2006/0135405 A1 | 6/2006 | Rischer et al. |
| 2006/0210639 A1 | 9/2006 | Liversidge et al. |
| 2007/0021357 A1 | 1/2007 | Tobia et al. |
| 2007/0021378 A1 | 1/2007 | Varki et al. |
| 2007/0060509 A1 | 3/2007 | Kanikanti et al. |
| 2007/0077313 A1 | 4/2007 | Krebs et al. |
| 2007/0148228 A1 | 6/2007 | Cumming et al. |
| 2007/0196464 A1 | 8/2007 | Cumming et al. |
| 2007/0212395 A1 | 9/2007 | Donello et al. |
| 2007/0219131 A1 | 9/2007 | Ben-Sasson |
| 2007/0238707 A1* | 10/2007 | Leonard .......................... 514/89 |
| 2007/0292512 A1 | 12/2007 | Leonard et al. |
| 2008/0171848 A1 | 7/2008 | Christiansen et al. |
| 2008/0213366 A1 | 9/2008 | Gowan, Jr. et al. |
| 2008/0275001 A1 | 11/2008 | Cumming et al. |
| 2009/0004281 A1 | 1/2009 | Nghiem et al. |
| 2009/0060861 A1 | 3/2009 | Poulsen |
| 2009/0274758 A1 | 11/2009 | Pinhasi et al. |
| 2009/0280169 A1 | 11/2009 | Leonard |
| 2009/0280170 A1 | 11/2009 | Lee et al. |
| 2010/0022480 A1 | 1/2010 | Leonard |
| 2010/0028421 A1 | 2/2010 | Cumming et al. |
| 2010/0105627 A1 | 4/2010 | Salama et al. |
| 2010/0209499 A1 | 8/2010 | Cumming et al. |
| 2010/0215743 A1 | 8/2010 | Leonard |
| 2010/0247640 A1 | 9/2010 | Leonard |
| 2011/0171140 A1 | 7/2011 | Illum et al. |
| 2011/0182985 A1 | 7/2011 | Coughlan et al. |
| 2012/0189692 A1 | 7/2012 | Cullen et al. |
| 2013/0089604 A1 | 4/2013 | Cumming et al. |

FOREIGN PATENT DOCUMENTS

| | | |
|---|---|---|
| CN | 101125132 | 2/2008 |
| EP | 0370481 A2 | 11/1989 |
| EP | 0376534 A1 | 7/1990 |
| EP | 0497162 A1 | 8/1992 |
| EP | 0517211 A1 | 12/1992 |
| EP | 0580074 A1 | 1/1994 |
| EP | 0747390 A2 | 12/1996 |
| EP | 0667148 B1 | 7/2002 |
| EP | 1246839 B1 | 6/2004 |
| EP | 1674082 A1 | 6/2006 |
| EP | 1339411 | 7/2007 |
| GB | 953626 | 3/1964 |
| GB | 2212396 A | 7/1989 |
| GB | 2336311 A | 10/1999 |
| IE | (11)63119 | 3/1995 |
| JP | 57-146722 | 10/1982 |
| JP | 59073600 | 4/1984 |
| JP | 62-283930 | 12/1987 |
| JP | 02180837 | 7/1990 |
| JP | 2282327 | 11/1990 |
| JP | 03275633 | 12/1991 |
| JP | 04149126 | 5/1992 |
| JP | 6040949 | 2/1994 |
| JP | 06192107 | 7/1994 |
| JP | 11035458 | 2/1999 |
| JP | 2002537321 | 11/2002 |
| JP | 2004529953 | 9/2004 |
| JP | 2004-533444 | 11/2004 |
| JP | 2006089496 | 4/2006 |
| RU | 2068689 | 11/1996 |
| WO | WO 84/04674 A1 | 12/1984 |
| WO | WO 93/05903 A1 | 4/1993 |
| WO | WO 93/09785 A1 | 5/1993 |
| WO | WO 93/21907 A1 | 11/1993 |
| WO | WO 94/08599 A1 | 4/1994 |
| WO | WO 94/10983 A1 | 5/1994 |
| WO | WO 95/22319 A1 | 8/1995 |
| WO | WO 95/34294 A1 | 12/1995 |
| WO | WO 97/05903 A2 | 2/1997 |
| WO | WO 97/44017 A1 | 11/1997 |
| WO | WO 98/01159 A2 | 1/1998 |
| WO | WO 99/01579 A1 | 1/1999 |
| WO | WO 99/02120 A2 | 1/1999 |
| WO | WO 99/02485 A1 | 1/1999 |
| WO | WO 99/18972 A1 | 4/1999 |
| WO | WO 99/45934 A1 | 9/1999 |
| WO | WO 00/22909 A2 | 4/2000 |
| WO | WO 00/50012 * | 8/2000 |
| WO | WO 00/50012 A1 | 8/2000 |
| WO | WO 00/61111 A1 | 10/2000 |
| WO | WO 01/82903 A1 | 11/2001 |
| WO | WO 01/89479 A2 | 11/2001 |
| WO | WO 02/20037 A1 | 3/2002 |
| WO | WO 02/064148 A2 | 8/2002 |
| WO | WO 02/087597 A1 | 11/2002 |
| WO | WO 02/092069 A1 | 11/2002 |
| WO | WO 02/092070 | 11/2002 |

(56) References Cited

FOREIGN PATENT DOCUMENTS

| | | |
|---|---|---|
| WO | WO 03/003999 A2 | 1/2003 |
| WO | WO 03/045419 A1 | 6/2003 |
| WO | WO 03/047493 A2 | 6/2003 |
| WO | WO 03/051373 A1 | 6/2003 |
| WO | WO 03/053401 A2 | 7/2003 |
| WO | WO 03053401 * | 7/2003 |
| WO | WO 03/072123 A1 | 9/2003 |
| WO | WO 2005/055973 A2 | 6/2005 |
| WO | WO 2005/063218 | 7/2005 |
| WO | WO 2005/072747 A1 | 8/2005 |
| WO | WO 2005/115331 A2 | 12/2005 |
| WO | WO 2006/010155 A2 | 1/2006 |
| WO | WO 2006/069641 A1 | 7/2006 |
| WO | WO 2006/097537 A2 | 9/2006 |
| WO | WO 2006/102117 A1 | 9/2006 |
| WO | WO 2006/103657 A1 | 10/2006 |
| WO | WO 2006/116565 A2 | 11/2006 |
| WO | WO 2007/117706 A2 | 10/2007 |
| WO | WO 2007/124090 A2 | 11/2007 |
| WO | WO 2009/137080 A1 | 11/2009 |
| WO | WO 2010/032140 A2 | 3/2010 |
| WO | WO 2010/099255 A1 | 9/2010 |
| WO | WO 2011/120033 A1 | 9/2011 |

OTHER PUBLICATIONS

Artursson, "Epithelial Transport of Drugs in Cell Culture. I: A Model for Studying the Passive Diffusion of Drugs over Intestinal Absorbtive (Caco-2) Cells," J Pharm Studies 79(7):476-482 (1990).
Aungst, "Structure/effect studies of fatty acid isomers as skin penetration enhancers and skin irritants," Pharm. Res. 6:244-247 (1989).
Aungst et al., "Enhancement of the intestinal absorption of peptides and non-peptides," J. Control. Release 41:19-31 (1996).
Baker et al., "Role of Body Surface Area in Dosing of Investigatioanl Agents in Adults, 1991-2001," J. Natl. Cancer Inst. 94:1883-1888 (2002).
Bennett et al., "Pulmonary Delivery of Detirelex by Intratracheal Instillation and Aerosol Inhalation in the Briefly Anesthetized Dog," Pharm. Res. 11:1048-1054 (1994).
Brayden et al., "Heparin Absorption Across the Intestine: Effects of Sodium N-[8-(2-Hydroxybenzoyl)Amino]Caprylate in Rat In Situ Intestinal Instillations and in Caco-2 Monolayers," Pharm. Res. 14(12):1772-1779 (1997).
Chan et al., "Depsipeptide (FR901228, NSC-630176) pharmacokinetics in the rat by LC/MS/MS," Invest. New Drugs 15:195-206 (1997).
Choay et al., "Structure-activity relationship in heparin: A synthetic pentasaccharide with high affinity for antithrombin III and eliciting high anti-factor Xa activity," Biochem. Biophys. Res. Commun. 116:492-499 (1983).
Cumming et al., "In vitro evaluation of a series of sodium carboxylates as dermal penetration enhancers," Int J Pharm 108:141-148 (1994).
Declaration of Dr. Thomas W. Leonard from European Patent Application EP 00905186.3.
Doluisio et al., "Drug Absorption I: An In Situ Rat Gut Technique Yielding Realistic Absorption Rates," J. Pharm. Studies 58(10):1196-1200 (1969).
Fernandez et al., "Comparative study on digestive lipase activities on the self emulsifying excipient Labrasol®, medium chain glycerides and PEG esters," Biochim. Biophys. Acta 1771:633-640 (2007).
Gennaro, "Remington: The Science and Practice of Pharmacy," 19th Edition, Mack Publishing Co., p. 1618 (1995).
Grohganz et al., "Development and in vitro evaluation of a liposome based implant formulation for the decapeptide cetrorelix," Eur. J. Pharm. Biopharm. 59:439-448 (2004).
Hahn, "Chemotherapy Dose Calculation and Administration in Exotic Animal Species," Sem. Avian Exotic Pet Med. 14:193-198 (2005).
Hild et al., "The ability of a gonadotropin-releasing hormone antagonist, acyline, to prevent irreversible infertility induced by the indenopyridine, CDB-4022, in adult male rats: the role of testosterone," Biol. Reproduction 71:348-358 (2004).
Jiang et al., "GnRH antagonists: a new generation of long acting analogues incorporating p-ureido-phenylalanines at positions 5 and 6," J. Med. Chem. 44:453-467 (2000).
Kajii et al., "Fluorescence study of the membrane-perturbing action of sodium caprylate as related to promotion of drug absorption," J. Pharm. Sci. 77:390-392 (1988).
Lesnyak, "Medicamental methods of treating osteoporosis," Gynecology, vol. 7 (2005); accessed at www.consilium-medicum.com/article/7685.
Lambent Technologies, "Technical Data Sheet for Lumulse L-4, Lumulse L-12, and Lumulse L-23", pp. 1-2 (2004).
Lambent Technologies, "Material Safety Data Sheet for Lumulse L-12", pp. 1-3 (2004).
Lindmark et al., "Mechanisms of Absorption Enhancement by Medium Chain Fatty Acids in Intestinal Epithelial Caco-2 Cell Monolayers," J. Pharmacol. Exp. Ther. 275(2):958-964 (1995).
Lindmark et al., "Mechanism of Absorption Enhancement in Humans After Rectal Administration of Ampicillin in Suppositories Containing Sodium Caprate," Pharm. Res. 14(7):930-935 (1997).
Massa et al., "3-(4-Aroyl-1H-pyrrol-2-yl)-N-hydroxy-2-propenamides, a New Class of Synthetic Histone Deacetylase Inhibitors," J. Med. Chem. 44:2069-2072 (2001).
"Mcgraw-Hill Dictionary of Chemical Terms", McGraw-Hill Book Company Ed. S.P. Parker, New York pp. 208, 209, 251 (1985).
Mechanick et al., "Effect of a Convenient Single 90-mg Pamidronate Dose on Biochemical Markers of Bone Metabolism in Patients With Acute Spinal Cord Injury," J. Spinal Cord Med. 29(4):406-412 (2006).
Mishima et al., "Studies on the Promoting Effects of Medium Chain Fatty Acid Salts on the Nasal Absorption of Insulin in Rats," J. Pharmacobio-Dyn. 10:624-631 (1987).
Moradei et al., "Histone deacetylase inhibitors: Latest developments, trends and prospects," Curr. Med. Chem. 5(5):529-560 (2005).
Morishita et al., "Site-Dependent Effect of Aprotinin, Sodium Caprate, Na2EDTA and Sodium Glycocholate on Intestinal Absorption of Insulin," Biol. Pharm. Bull. 16:68-72 (1993).
Murakami et al., "Effect of Oleic Acid Vesicles on Intestinal Absorption of Carboxyfluorescein in Rats", Pharm. Res. 3(1):35-40 (1986).
Muranishi, "Absorption Enhancers," Crit. Rev. Ther. Drug Carrier Systems 7:1-33 (1990).
Muranushi et al., "The Effects of Fatty Acids and Their Derivatives on the Intestinal Absorption of Insulin in Rat," Drug Dev. Indust. Pharm. 19(8):929-941 (1993).
Octreotide, Wikipedia. Printed Mar. 23, 2009. 3 pp.
Oda (Inamori), "Absorption Enhancement of Argatroban by Medium Chain Fatty Acid Sodium Salts," Proceedings Int'l Symp. Control. Rel. Bioact. Mater. 24:283-284 (1997).
Palin et al., "The oral absorption of cefoxitin from oil and emulsion vehicles in rats," Int. J. of Pharmaceutics 33:99-104 (1986).
Poster Presentation entitled "A Phase I Trial and Pharmacokinetic Study of Depsipeptide in Pediatric Patients with Refractory Solid Tumors: A Children's Oncology Group Study" at American Society of Clinical Oncology meeting, May 2005, abstract 8528 (Fouladi et al.).
Sawada et al., "Role of Paracellular Pathway in Nonelectrolyte Permeation Across Rat Colon Epithelium Enhanced by Sodium Caprate and Sodium Caprylate," Pharm. Res. 8(11):1365-1371 (1991).
Sawyer et al., "Body surface area as a determinant of pharmacokinetics and drug dosing," Invest. New Drugs 19:171-177 (2001).
Schneider et al., "Evaluation of drug penetration into human skin ex vivo using branched fatty acids and propylene glycol," Int. J. Pharm. 145:187-196 (1996).
Sikora, "Cancer drug development in the post-genomic age," Curr. Sci. 81:549-54 (2001).
Sinko, "Martin's Physical Pharmacy and Pharmaceutical Sciences," 5$^{th}$ Ed., Lippincott Williams & Wilkins, 355-357 (2006).
Somatostatin, Wikipedia. Printed Mar. 23, 2009. 4 pp.
Tomita et al., "Absorption-Enhancing Mechanism of Sodium Caprate and Decanoylcarnitine in Caco-2 Cells," J. Pharmacol. Exp. Ther. 272(2):739-743 (1995).

(56) References Cited

OTHER PUBLICATIONS

Tomita et al., "Enhancement of Colonic Drug Absorption by the Transcellular Permeation Route," Pharm. Res. 5(12):786-789 (1988).

Tomita et al., "Enhancement of Colonic Drug Absorption by the Paracellular Permeation Route," Pharm. Res. 5(6):341-346 (1988).

Tomita et al., "Differences in the Enhancing Effects of Sodium Caprate on Colonic and Jejunal Drug Absorption," Pharm. Res. 9(5):648-653 (1992).

WPI Database, Accession No. 1984-142694, English language abstract of JP 59073600.

WPI Database, Accession No. 1992-028863, English language abstract of JP 03275633.

WPI Database, Accession No. 1997-287727, English language abstract of RU 2068689.

Yamamoto et al., "Pulmonary absorption enhancement of peptides by absorption enhancers and protease inhibitors," J. Control. Release 41:57-67 (1996).

Yang et al., Deposition of insulin powders for inhalation in vitro and pharmacodynamic evaluation of absorption promoters in rats, Acta Pharmaceutica Sinica 40:1069-1074 (2005).

Yeh et al., "Effect of Medium-Chain Glycerides on Physiological Properties of Rabbit Intestinal Epithelium in Vitro," Pharm. Res. 11(8):1148-1154 (1994).

Zhou et al., "Effects of cholic acid and other enhancers on the bioavailability of insulin from a subcutaneous site," Int. J. Pharm. 69:29-41 (1991).

Zips et al., "New anticancer agents: In vitro and in vivo evaluation," In vivo 19:108 (2005).

U.S. Appl. No. 09/510,560, filed Feb. 22, 2000; Office Action mailed Mar. 26, 2001.

U.S. Appl. No. 09/510,560, filed Feb. 22, 2000; Office Action mailed Jul. 15, 2002.

U.S. Appl. No. 09/510,560, filed Feb. 22, 2000; Office Action mailed Oct. 22, 2003.

U.S. Appl. No. 09/510,560, filed Feb. 22, 2000; Office Action mailed Jun. 4, 2004.

U.S. Appl. No. 09/510,560, filed Feb. 22, 2000; Office Action mailed May 18, 2005.

U.S. Appl. No. 09/510,560, filed Feb. 22, 2000; Office Action mailed Nov. 21, 2005.

U.S. Appl. No. 09/510,560, filed Feb. 22, 2000; Office Action mailed Jun. 14, 2006.

U.S. Appl. No. 09/510,560, filed Feb. 22, 2000; Office Action mailed Dec. 15, 2006.

U.S. Appl. No. 09/510,560, filed Feb. 22, 2000; Office Action mailed Aug. 23, 2007.

U.S. Appl. No. 09/510,560, filed Feb. 22, 2000; Office Action mailed Feb. 20, 2008.

U.S. Appl. No. 09/510,560, filed Feb. 22, 2000; Office Action mailed Sep. 17, 2008.

U.S. Appl. No. 09/510,560, filed Feb. 22, 2000; Office Action mailed May 27, 2009.

U.S. Appl. No. 11/400,689, filed Apr. 7, 2006; Office Action mailed Feb. 12, 2009.

U.S. Appl. No. 11/450,641, filed Jun. 9, 2006; Office Action mailed Jun. 25, 2009.

U.S. Appl. No. 11/450,641, filed Jun. 9, 2006; Office Action mailed Apr. 14, 2010.

U.S. Appl. No. 12/172,707, filed Jul. 14, 2008; Office Action mailed Jan. 4, 2011.

U.S. Appl. No. 12/172,707, filed Jul. 14, 2008; Office Action mailed Apr. 27, 2011.

U.S. Appl. No. 12/553,196, filed Sep. 3, 2009; Office Action mailed Sep. 24, 2010.

U.S. Appl. No. 12/553,196, filed Sep. 3, 2009; Office Action mailed Mar. 31, 2011.

U.S. Appl. No. 12/768,008, filed Apr. 27, 2010; Office Action mailed Aug. 2, 2011.

U.S. Appl. No. 11/733,007, filed Apr. 9, 2007; Office Action mailed Jan. 29, 2009.

U.S. Appl. No. 11/733,007, filed Apr. 9, 2007; Office Action mailed Aug. 17, 2009.

U.S. Appl. No. 12/481,952, filed Jun. 10, 2009; Office Action mailed Jul. 26, 2011.

U.S. Appl. No. 11/761,233, filed Jun. 11, 2007; Office Action mailed Sep. 1, 2009.

U.S. Appl. No. 11/761,233, filed Jun. 11, 2007; Office Action mailed Jun. 28, 2010.

U.S. Appl. No. 12/436,990, filed May 7, 2009; Office Action mailed Sep. 14, 2010.

U.S. Appl. No. 12/436,990, filed May 7, 2009; Office Action mailed Mar. 16, 2011.

International Application No. PCT/US2011/030159, filed Mar. 28, 2011, international search report and written opinion.

International Search Report Corresponding to International Application No. PCT/US11/30159; Date of Mailing: May 23, 2011; 11 pages.

Motlekar, "Oral delivery of low-molecular-weight heparin using sodium caprate as absorption enhancer reaches therapeutic levels," J. Drug Targeting 13(10):573-583 (2005).

Tanaka et al. "Enhancement of intestinal transport of thyrotropin-releasing hormone via a carrier-mediated transport system by chemical modification with lauric acid," Biochim. Biophys. Acta 1283:119-126 (1996).

Yamamoto et al., "Improvement of intestinal absorption of peptide and protein drugs by chemical modification, with fatty acids," Nihon Rinsho 56(3):601-607 (1998).

U.S. Appl. No. 11/450,641, filed Jun. 9, 2006; Office Action mailed Nov. 9, 2011.

U.S. Appl. No. 12/172,707, filed Jul. 14, 2008; Office Action mailed Nov. 9, 2011.

U.S. Appl. No. 12/481,952, filed Jun. 10, 2009; Office Action mailed Nov. 23, 2011.

U.S. Appl. No. 12/436,990, filed May 7, 2009; Office Action mailed Oct. 7, 2011.

U.S. Appl. No. 13/242,601, filed Sep. 23, 2011.

Abrahamson et al., "Synthesis and characterization of iron stearate compounds," J. Inorg. Chem. 54:115-130 (1994).

Cosman et al., "Clinical evaluation of novel bisphosphonate dosing regimens in osteoporosis: The role of comparative studies and implications for future studies," Clin. Ther. 29:1116-1127 (2007).

Drummond et al., "Clinical development of histone deacetylase inhibitors as anticancer agents," Annu. Rev. Pharmacol. Toxicol. 45:495-528 (2005).

European Food Safety Authority, "Scientific opinion on the use of ferric sodium EDTA as a source of iron added for nutritional purposes to foods for the general population (including food supplements) and to foods for particular nutritional uses," EFSA J. 8:1414 (2010).

Kishimoto et al, "Efficacy and tolerability of once-weekly administration of 17.5mg risedronate in Japanese patients with involutional osteoporosis: a comparison with 2.5-mg once-daily dosage regimen," J. Bone Miner. Metab. 24:405-413 (2006).

Schnitzer et al., "Therapeutic equivalence of alendronate 70 mg once-weekly and alendronate 10 mg daily in the treatment of osteoporosis," Aging Clin. Exp. Res. 12:1-12 (2000).

Simpson et al., "Significance of non-esterified fatty acids in iron uptake by intestinal brush-border membrane vesicles," Biochim. Biophys. Acta 941:39-47 (1988).

U.S. Appl. No. 12/172,707, filed Jul. 14, 2008; Office Action mailed Feb. 21, 2012.

U.S. Appl. No. 12/768,008, filed Apr. 27, 2010; Office Action mailed Feb. 29, 2012.

U.S. Appl. No. 12/767,076, filed Apr. 26, 2010; Office Action mailed Feb. 9, 2012.

U.S. Appl. No. 12/767,076, filed Apr. 26, 2010; Office Action mailed May 31, 2012.

U.S. Appl. No. 12/437,012, filed May 7, 2009; Office Action mailed Mar. 6, 2012.

U.S. Appl. No. 12/437,012, filed May 7, 2009; Office Action mailed Nov. 27, 2012.

(56) References Cited

OTHER PUBLICATIONS

U.S. Appl. No. 12/712,527, filed Feb. 25, 2010; Office Action mailed Sep. 26, 2012.
U.S. Appl. No. 13/345,185, filed Jan. 6, 2012; Office Action mailed Feb. 13, 2013.
Hovgaard, "Insulin stabilization and gastrointestinal absorption," Ph.D. thesis, pp. 1-218 (1991).
Maher at al., "Safety and efficacy of sodium caprate in promoting oral drug absorption: from in vitro to the clinic," Adv. Drug Del. Rev. 61:1427-1449 (2009).
U.S. Appl. No. 12/481,952, filed Jun. 10, 2009; Office Action mailed Apr. 3, 2014.
U.S. Appl. No. 12/767,076, filed Apr. 26, 2010; Office Action mailed Mar. 24, 2014.
U.S. Appl. No. 12/436,990, filed May 7, 2009; Office Action mailed Mar. 4, 2014.
U.S. Appl. No. 12/437,012, filed May 7, 2009; Office Action mailed Feb. 26, 2014.
U.S. Appl. No. 13/014,156, filed Jan. 26, 2011; Office Action mailed Apr. 11, 2014.
Bird, "Genetic aspects of Alzheimer disease," Genet. Med. 10:231-239 (2008).
Breddin, "The role of antithrombin agents and Factor Xa-inhibitors in antithrombotic treatment," Turk. J. Haematol. 19:113-120 (2002).
Herbst, "Gonadotropin-releasing hormone antagonists," Curr. Opin. Pharmacol. 3:660-666 (2003).
Jiang et al., "Betidamino acid scan of the GnRH antagonist acyline," J. Med. Chem. 40:3739-3748 (1997).
Kalweit et al., "Pulmonary embolism: a frequent cause of acute fatality after lung resection," Eur. J. Cardio-thorac. Surg. 10:242-247 (1996).
Kleinebudde, "Roll compaction/dry granulation: pharmaceutical applications," Eur. J. Pharm. Biopharm. 58:317-326 (2004).
Tak et al., "The pathogenesis and prevention of joint damage in rheumatoid arthritis," Arthritis Rheumatism 43:2619-2633 (2000).
Wood-Kaczmar et al., "Understanding the molecular causes of Parkinson's disease," Trends Mel. Med. 12:521-528 (2006).
U.S. Appl. No. 13/690,082, filed Nov. 30, 2012; Office Action mailed Oct. 29, 2013.
U.S. Appl. No. 13/014,156, filed Jan. 26, 2011; Office Action mailed Jun. 6, 2013.
U.S. Appl. No. 12/437,012, filed May 7, 2009; Office Action mailed Jul. 16, 2013.
U.S. Appl. No. 12/712,527, filed Feb. 25, 2010; Office Action mailed May 20, 2013.
U.S. Appl. No. 13/345,185, filed Jan. 6, 2012; Office Action mailed Jul. 30, 2013.
U.S. Appl. No. 13/242,601, filed Sep. 23, 2011; Office Action mailed Jun. 4, 2013.
U.S. Appl. No. 13/242,601, filed Sep. 23, 2011; Office Action mailed Dec. 17, 2013.
Goodnough et al., "Erythropoietin, iron, and erythropoiesis," Blood 96:823-833 (2000).
Vetter et al., "Development and in vivo availability study of an oral fondaparinux delivery system," Eur. J. Pharm. Sci. 41:489-497 (2010).
U.S. Appl. No. 12/436,990, filed May 7, 2009; Office Action mailed Jul. 10, 2014.
Cullen et al., "Oral delivery of fondaparinux: A potential patient benefit in thrombosis therapy," Poster presentation at the 2010 AAPS Annual Meeting and Exposition; Nov. 14-18, 2010, New Orleans, Poster W4066.
Fatty Acids: Straight-Chain Saturated, downloaded from http://lipidlibrary.aocs.org/Lipids/fa_sat/index.htm on Nov. 21, 2014.
Leonard et al., "Promoting absorption of drugs in humans using medium-chain fatty acid-based solid dosage forms: GIPET," Expert Opin. Drug Deliv. 3:685-692 (2006).
U.S. Appl. No. 12/436,990, filed May 7, 2009; Office Action mailed Nov. 24, 2014.
U.S. Appl. No. 13/242,601, filed Sep. 23, 2011; Office Action mailed Nov. 12, 2014.
Leonard et al., MER-101 tablets: A bioavailability study of a novel oral formulation of zoledronic acid, Oct. 24, 2007, printed from http://www.merrionpharma.com/archive/mer101_poster_eortc.24oct07.pdf, Google date sheet of entry into the internet included, 2 pages.
Lin et al., "Release-controlling absorption enhancement of enterally administered *Ophiopogon japonicus* polysaccharide by sodium caprate in rats," J. Pharm. Sci. 95:2534-2542 (2006).
U.S. Appl. No. 13/014,156 filed Jan. 26, 2011; Office Action mailed Jan. 13, 2015.
U.S. Appl. No. 12/712,527 filed Feb. 25, 2010; Office Action mailed Mar. 31, 2015.

* cited by examiner

PHARMACEUTICAL COMPOSITIONS OF SELECTIVE FACTOR XA INHIBITORS FOR ORAL ADMINISTRATION

This application claims the benefit of U.S. Provisional Application Ser. Nos. 61/317,961 filed Mar. 26, 2010 and 61/423,261 filed Dec. 15, 2010, the disclosure of each of which is incorporated by reference herein in its entirety.

FIELD OF THE INVENTION

The present invention generally relates to orally administered pharmaceutical compositions of selective factor Xa inhibitors.

BACKGROUND OF THE INVENTION

Today, anticoagulants are widely used to prevent and treat a variety of thromboembolic events. Currently, available anticoagulants for treatment include unfractionated heparin (UFH), low molecular weight heparin (LMWH), and vitamin K antagonists (VKAs) (e.g., warfarin). More recently, synthetic pentasaccharides (e.g., fondaparinux (Arixtra®)) have also been developed as effective anticoagulants. The advantage of fondaparinux over LMWH or UFH is that the risk for heparin-induced thrombocytopenia is substantially reduced as fondaparinux inhibits factor Xa via binding to antithrombin III and does not inhibit thrombin or possess other activities of heparin.

Although anticoagulants are effective in treating and reducing the risk of thromboembolic disease, they are associated with significant drawbacks that limit their use and acceptability in the clinical setting. The traditional anticoagulants are administered parenterally and require frequent monitoring and subsequent dose adjustment. For example, UFH, LMWH, and fondaparinux are administered parenterally, which is inconvenient and expensive for long-term use, particularly outside of the hospital setting where visits to or from a health care professional may be required. Vitamin K antagonists are the only available oral anticoagulants. However, they usually have a narrow therapeutic window and unpredictable pharmacology, and require close monitoring and dose adjustment to ensure that anticoagulant effects remain within the therapeutic range.

Different approaches have been proposed to develop orally administered anticoagulants. One approach is to develop small molecule direct factor Xa inhibitors. Unlike the more traditional anticoagulants (UFH, LMWH, and VKAs) that target multiple enzymes in the coagulation cascade, the new drugs inhibit single enzymes. Currently, several oral factor Xa inhibitors are in clinical development, such as rivaroxaban (Bayer HealthCare AG and Scios, Inc.), apixaban (Bristol-Myers Squibb), and 813893 (GlaxoSmithKline).

Despite the recent promising development of direct factor Xa inhibitors, there is a continuing need for development of novel pharmaceutical formulations of selective factor Xa inhibitors suitable for oral administration, which not only offer the convenience of oral dosing, but also provide a reproducible and predictable bioavailability of the active ingredient.

SUMMARY OF THE INVENTION

The present invention provides a pharmaceutical composition for oral administration comprising a therapeutically effective amount of a selective factor Xa inhibitor or a pharmaceutically acceptable salt thereof and an enhancer, wherein the enhancer is a medium chain fatty acid or a salt, ester, ether, or derivative of a medium chain fatty acid and has a carbon chain length of from about 4 to about 20 carbon atoms. In some embodiments, the selective factor Xa inhibitor is fondaparinux or a pharmaceutically acceptable salt thereof.

Another aspect of the present invention provides a method of treating or preventing a medical condition, comprising administering to a subject in need of treatment or prevention a therapeutically effective amount of a selective factor Xa inhibitor or a pharmaceutically acceptable salt thereof together with an enhancer, wherein the enhancer is a medium chain fatty acid or a salt, ester, ether, or derivative of a medium chain fatty acid and has a carbon chain length of from about 4 to about 20 carbon atoms.

Another aspect of the present invention provides a process for manufacturing a solid oral dosage form of a pharmaceutical composition comprising the steps of: a) blending a selective factor Xa inhibitor or a pharmaceutically acceptable salt thereof with an enhancer, and optionally additional excipients, to form a blend; wherein the enhancer is a medium chain fatty acid or a salt, ester, ether, or derivative of a medium chain fatty acid and has a carbon chain length of from about 4 to about 20 carbon atoms; and b) forming a solid oral dosage form from the blend by i) directly compressing the blend to form the solid oral dosage form, or ii) granulating the blend to form a granulate for incorporation into the solid oral dosage form, or iii) spray drying the blend to form a multiparticulate for incorporation into the solid oral dosage form.

Another aspect of the present invention provides a pharmaceutical composition of a selective factor Xa inhibitor or a pharmaceutically acceptable salt thereof for oral administration in the form of a stable, transparent drug delivery composition, wherein the drug delivery composition comprises (a) from about 1 to about 80 weight percent of a pharmaceutically acceptable oil; (b) from about 3 to about 98 weight percent (e.g., from about 3 to about 96.5 weight percent) surface active agents; (c) from about 2 to about 60 weight percent polyethylene glycol; and (d) from about 0.5 to about 15 weight percent water; wherein the ratio of the polyethylene glycol to water is at least 2:1.

One aspect of the present invention describes a pharmaceutical composition of a selective factor Xa inhibitor or a pharmaceutically acceptable salt thereof for oral administration which is an emulsion composition, wherein an internal phase of the emulsion composition contains a therapeutically effective amount of a selective factor Xa inhibitor or a pharmaceutically acceptable salt thereof; and the internal phase comprises a polar, nonaqueous, oxygen-containing, pharmaceutically acceptable liquid selected from the group consisting of $C_2$-$C_{30}$ polyhydric alcohols, poly(ethylene or propylene)glycols with 4-200 repeating units, $C_2$-$C_{30}$ ester derivatives thereof, and $C_1$-$C_5$ ether derivatives thereof.

Another aspect of the present invention provides a pharmaceutical composition of a selective factor Xa inhibitor for oral administration which is a water-in-oil microemulsion composition, wherein the microemulsion composition converts to an oil-in-water emulsion by the addition of water and the microemulsion composition comprises (a) up to about 20 volume percent of an internal dispersed aqueous phase containing a therapeutically effective amount of a selective factor Xa inhibitor or a pharmaceutically acceptable salt thereof, (b) from about 30 to about 99 volume percent of a continuous oil phase comprising mono and di-esters of propylene glycol having from about 15 to about 40 carbon atoms, and (c) from about 1 to about 70 volume percent of a surfactant or mixture of surfactants, wherein the surfactant or surfactant mixture has a hydrophilic-lipophilic balance (HLB) value of from 7 to 14.

One aspect of the present invention describes a pharmaceutical composition of a selective factor Xa inhibitor for oral administration which is a water-in-oil microemulsion composition, wherein the microemulsion composition converts to an oil-in-water emulsion by the addition of water and the microemulsion composition comprises (a) up to about 60 volume percent, based upon the total volume of the microemulsion, of an internally dispersed aqueous phase containing a therapeutically effective amount of a selective factor Xa inhibitor or a pharmaceutically acceptable salt thereof; (b) from about 5 to about 90 volume percent of a continuous oil phase comprising at least one pharmaceutically acceptable oil; and (c) from 1 to about 70 volume percent of a surfactant or mixture of surfactants, wherein the surfactant or surfactant mixture has a HLB value of from 7 to 14.

Another aspect of the present invention provides a pharmaceutical composition of a selective factor Xa inhibitor for oral administration which is a water-in-oil microemulsion composition, wherein the microemulsion composition comprises (a) from about 5 to about 99 volume percent of an oil phase comprising at least one pharmaceutically acceptable oil; (b) up to about 60 volume percent of an aqueous phase comprising water; (c) a therapeutically effective amount of a selective factor Xa inhibitor or a pharmaceutically acceptable salt thereof; (d) from about 1 to about 70 volume percent of a mixture of surfactants having a combined HLB value of from about 7 to about 14 comprising (i) a low HLB surfactant having a HLB below 8, said low HLB surfactant being at least 40 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surfactant having a HLB value above about 8.

One aspect of the present invention provides a pharmaceutical composition of a selective factor Xa inhibitor for oral administration which is a water-in-oil microemulsion composition, wherein the microemulsion composition comprises (a) up to about 60 volume percent of an internal dispersed aqueous phase containing a therapeutically effective amount of a selective factor Xa inhibitor or a pharmaceutically acceptable salt thereof; (b) from about 5 to about 99 volume percent of a continuous oil phase comprising at least one pharmaceutically acceptable oil comprising a $C_{9-83}$ triglyceride, a $C_{7-55}$ mono- and di-ester of propylene glycol, or mixtures thereof; and (c) from about 1 to about 70 volume percent of a surfactant or surfactant mixture comprising a $C_8$ fatty acid salt, wherein the surfactant or surfactant mixture has a HLB value of at least 7.

Another aspect of the present invention provides a method for obtaining a reproducible bioavailability of a selective factor Xa inhibitor in a subject after oral administration, comprising orally administering a pharmaceutical composition of the invention to said subject.

DETAILED DESCRIPTION

Figure 1:
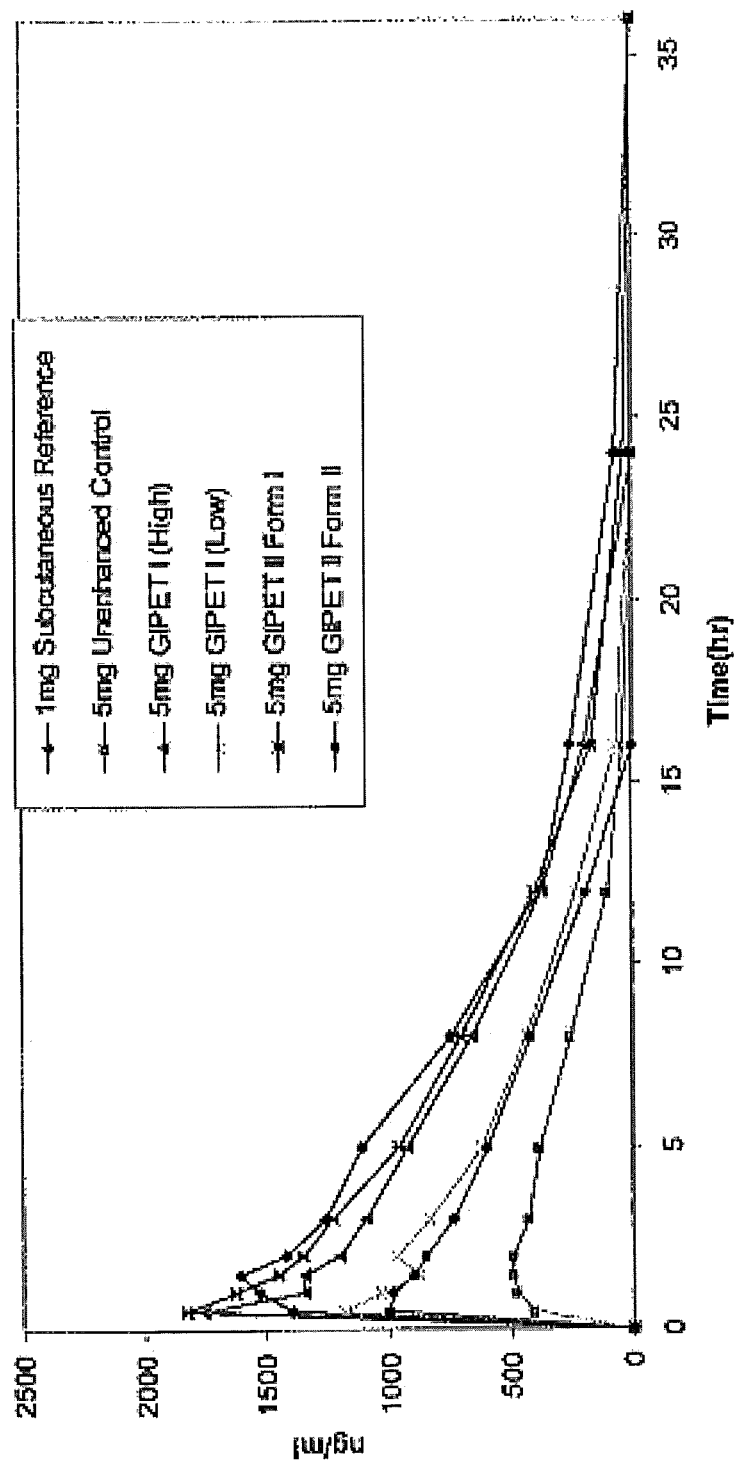
FIG. 1 shows the plasma concentration levels of different GIPET™ ("Gastrointestinal Permeation Enhancement Technology") formulations of fondaparinux in dogs following intraduodenal administration.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

All patents, patent applications and publications referred to herein are incorporated by reference in their entirety. In case of a conflict in terminology, the present specification is controlling.

The terminology used in the description of the invention herein is for the purpose of describing particular embodiments only and is not intended to be limiting of the invention.

As used in the description of the embodiments of the invention and the appended claims, the singular forms "a", "an" and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

Unless the context indicates otherwise, it is specifically intended that the various features of the invention described herein can be used in any combination. For example, features described in relation to one embodiment may also be applicable to and combinable with other embodiments and aspects of the invention.

Moreover, the present invention also contemplates that in some embodiments of the invention, any feature or combination of features set forth herein can be excluded or omitted.

The term "tablet" as used herein includes, but is not limited to, immediate release (IR) tablets, sustained release (SR) tablets, matrix tablets, multilayer tablets, multilayer matrix tablets, extended release tablets, delayed release tablets and pulsed release tablets any or all of which may optionally be coated with one or more coating materials, including polymer coating materials, such as enteric coatings, rate-controlling coatings, semi-permeable coatings and the like. The term "tablet" also includes osmotic delivery systems in which a drug compound is combined with an osmagent (and optionally other excipients) and coated with a semi-permeable membrane, the semi-permeable membrane defining an orifice through which the drug compound may be released. Tablet solid oral dosage forms that may be useful in the practice of the invention include those selected from the group consisting of IR tablets, SR tablets, coated IR tablets, coated SR tablets, matrix tablets, coated matrix tablets, multilayer tablets, coated multilayer tablets, multilayer matrix tablets and coated multilayer matrix tablets. In some embodiments, a tablet dosage form is an enteric-coated tablet dosage form. In some embodiments, a tablet dosage form is an enteric-coated rapid onset tablet dosage form.

Capsule solid oral dosage forms that may be useful in the practice of the present invention include those selected from the group consisting of IR capsules, SR capsules, coated IR capsules, and coated SR capsules including delayed release capsules. Capsules may be filled with powders, granules, multiparticulates, tablets, semi-solids, or liquids. In some embodiments, a capsule dosage form is an enteric-coated capsule dosage form. In some embodiments, a capsule dosage form is an enteric-coated rapid onset capsule dosage form. Capsules may be made of hard gelatin, soft gelatin, starch, cellulose polymers, or other materials as known to the art.

The term "multiparticulate" as used herein means a plurality of discrete particles, pellets, mini-tablets and mixtures or combinations thereof. If the oral form is a multiparticulate capsule, hard or soft gelatin capsules or capsules of other materials can suitably be used to contain the multiparticulate. In some embodiments, a sachet can suitably be used to contain the multiparticulate. In some embodiments, the multiparticulate may be coated with a layer containing rate controlling polymer material. In some embodiments, a multiparticulate oral dosage form according to the invention may comprise a blend of two or more populations of particles, pellets, or mini-tablets having different in vitro and/or in vivo release characteristics. For example, a multiparticulate oral dosage form may comprise a blend of an instant release component and a delayed release component contained in a suitable capsule.

In some embodiments, the multiparticulate and one or more auxiliary excipient materials can be compressed into tablet form such as a multilayer tablet. In some embodiments, a multilayer tablet may comprise two layers containing the same or different levels of the same active ingredient having the same or different release characteristics. In some embodiments, a multilayer tablet may contain different active ingredient in each layer. Such a tablet, either single layered or multilayered, can optionally be coated with a controlled release polymer so as to provide additional controlled release properties. In some embodiments, multiparticulate dosage form comprises a capsule containing delayed release rapid onset minitablets. In some embodiments, a multiparticulate dosage form comprises a delayed release capsule comprising instant release minitablets. In some embodiments, a multiparticulate dosage form comprises a capsule comprising delayed release granules. In some embodiments, a multiparticulate dosage form comprises a delayed release capsule comprising instant release granules.

The term "emulsion" as used herein means a suspension or dispersion of one liquid within a second immiscible liquid. In some embodiments, the emulsion is an oil-in-water or water-in-oil-in-water emulsion.

The term, "microemulsion" as used herein means a solution in which the hydrophobic (oil-like) phase and the hydrophilic (water-like) phase and a surfactant form micelle structures. Such dispersions are clear and stable over time. In certain embodiments, the micelles have an average diameter of about 1 micron or less.

In addition, "emulsion" or "microemulsion" as used herein includes a hydrophilic or a hydrophobic liquid which, on dilution with a hydrophobic or a hydrophilic liquid respectively, forms an emulsion or a microemulsion. In some embodiments, "emulsion" or "microemulsion" as used herein may include solid or semi-solid materials which may be liquid at higher temperatures. For example, the material may be solid at room temperature. At about body temperature (about 37° C.), the material may be liquid.

By the terms "treat," "treating," or "treatment of" (and grammatical variations thereof) it is meant that the severity of the subject's condition is reduced, at least partially improved, or stabilized and/or that some alleviation, mitigation, decrease, or stabilization in at least one clinical symptom and/or parameter is achieved and/or there is a delay in the progression of the disease or disorder.

The terms "prevent," "preventing," and "prevention" (and grammatical variations thereof) refer to avoidance, prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

An "effective amount," as used herein, refers to an amount that imparts a desired effect, which is optionally a therapeutic or prophylactic effect.

A "treatment effective" amount, as used herein, is an amount that is sufficient to provide some improvement or benefit to the subject. Alternatively stated, a "treatment effective" amount is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

A "prevention effective" amount, as used herein, is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

As used herein, a "therapeutically effective" or "therapeutically acceptable" amount refers to an amount that will elicit a therapeutically useful response in a subject. The therapeutically useful response may provide some alleviation, mitigation, or decrease in at least one clinical symptom in the subject. The terms also include an amount that will prevent or delay at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

"Subjects" according to the present invention include mammals, avians, reptiles, amphibians, and fish. Mammalian subjects include but are not limited to humans, non-human mammals, non-human primates (e.g., monkeys, chimpanzees, baboons, etc.), dogs, cats, mice, hamsters, rats, horses, cows, pigs, rabbits, sheep and goats. Avian subjects include but are not limited to chickens, turkeys, ducks, geese, quail and pheasant, and birds kept as pets (e.g., parakeets, parrots, macaws, cockatoos, and the like). In particular embodiments, the subject is from an endangered species. In particular embodiments, the subject is a laboratory animal. Human subjects include neonates, infants, juveniles, adults, and geriatric subjects. In certain embodiments, the subject is in need of the methods of the present invention, e.g., has a thromboembolic disorder. In other embodiments, the subject has, may have, or is at risk for a thromboembolic disorder.

"Stable," as used herein with respect to pharmaceutical compositions, refers to a composition that degrades no more than 10% when stored for one month at −20° C., e.g., at 4° C., e.g., at room temperature, and a relative humidity of 20% to 80%.

"Reproducible," as used herein, refers to pharmacokinetic characteristics of the pharmaceutical compositions of the invention that are consistent from subject to subject. A reproducible pharmacokinetic characteristic, e.g., bioavailability, $C_{max}$, or AUC, is one that has a coefficient of variation of less than about 60%, e.g., less than about 60, 55, 50, 45, 40, 35, 30, 25, 20, or 15% or less.

As used herein, a "derivative of a medium chain fatty acid" refers to a fatty acid derivative having at least one carbon chain of from 4 to 20 carbon atoms in length. This carbon chain may be characterized by various degrees of saturation. In other words, the carbon chain may be, for example, fully saturated or partially unsaturated (i.e., containing one or more carbon-carbon multiple bonds). The term "fatty acid derivative" is meant to encompass acyl derivatives such as esters, acid halides, anhydrides, amides and nitrites, and also ethers and glycerides such as mono-, di- or tri-glycerides. The term "fatty acid derivative" is meant to further encompass medium chain fatty acids wherein the end of the carbon chain opposite the acid group (or derivative) is also functionalized with one of the above mentioned moieties (i.e., ester, acid halide, anhydride, amide, nitrile, ether and glyceride moieties). Such difunctional fatty acid derivatives thus include for example diacids and diesters (the functional moieties being of the same kind) and also difunctional compounds comprising different functional moieties, such as amino acids and amino acid derivatives (for example a medium chain fatty acid, or an ester or a salt thereof, comprising an amide moiety at the opposite end of the fatty acid carbon chain to the acid (or ester or salt thereof).

The present invention provides a pharmaceutical composition for oral administration comprising, consisting essentially of, or consisting of a therapeutically effective amount of a selective factor Xa inhibitor or a pharmaceutically acceptable salt thereof and an enhancer, wherein the enhancer is a medium chain fatty acid or a salt, ester, ether, or derivative of a medium chain fatty acid and has a carbon chain length of from about 4 to about 20 carbon atoms. In certain embodiments, the medium chain fatty acid enhancer is the only enhancer present in the composition.

The present invention provides a solid oral dosage comprising, consisting essentially of, or consisting of the pharmaceutical composition of the invention. In certain embodiments, the solid oral dosage form is a tablet, a multiparticulate, or a capsule.

In some embodiments, the selective factor Xa inhibitor is an oligosaccharide. In another embodiment, the selective factor Xa inhibitor is a pentasaccharide. In some embodiments, the selective factor Xa inhibitor is fondaparinux or a pharmaceutically acceptable salt thereof.

As used herein, "selective factor Xa inhibitor" refers to a compound which selectively inhibits factor Xa directly or indirectly (e.g., via antithrombin III) but does not possess a significant activity towards thrombin. The term "does not possess a significant activity" refers to a compound that reduces thrombin activity by less than 20%, e.g., less than 15%, 10%, or 5%. In some embodiments, the selective factor Xa inhibitor possesses no inhibitory activity towards thrombin. Exemplary synthetic selective factor Xa inhibitors include, but are not limited to, fondaparinux and pharmaceutically acceptable salts thereof (the structure of fondaparinux is shown below), antistasin, tick anticoagulant peptide, yagin, apixaban, otamixaban, rivaroxaban, NAP-5, TAP, rNAPc-2, TFPI, DX-9065a, YM-60828, RPR-120844, BX-807834, and compounds described in EP 84999, EP 529715, EP 621282, U.S. Pat. Nos. 6,541,488, 6,391,339, 6,369,080, 6,262,047, and 6,133,256, and U.S. Published Application No. 2006/0122151, which are incorporated by reference in their entireties.

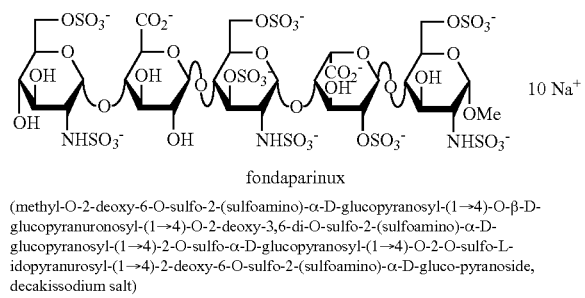

fondaparinux
(methyl-O-2-deoxy-6-O-sulfo-2-(sulfoamino)-α-D-glucopyranosyl-(1→4)-O-β-D-glucopyranuronosyl-(1→4)-O-2-deoxy-3,6-di-O-sulfo-2-(sulfoamino)-α-D-glucopyranosyl-(1→4)-2-O-sulfo-α-D-glucopyranosyl-(1→4)-O-2-O-sulfo-L-idopyranurosyl-(1→4)-2-deoxy-6-O-sulfo-2-(sulfoamino)-α-D-gluco-pyranoside, decakissodium salt)

A salt of a selective factor Xa inhibitor may be prepared by combining the compound in its free acid or base form with a suitable organic or inorganic acid or base and isolating the salt thus formed. For example, when the selective factor Xa inhibitor is fondaparinux (in the sodium salt form), the salt is formed by reacting the free acid form of fondaparinux with a suitable inorganic or organic base. The term "pharmaceutically acceptable salt" refers to a relatively non-toxic, inorganic or organic acid or base addition salt of a compound of the present invention (see, e.g., Berge et al., J. Pharm. Sci. 66:1-19, 1977).

Representative salts of the compounds of the present invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, undecanoate, and the like.

Base salts include, for example, alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups in the conjugate base may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides; aralkyl halides like benzyl and phenethyl bromides, and the like.

In some embodiments, the enhancer is a salt of a medium chain fatty acid which has a carbon chain length of from 6 to 20 carbon atoms. In some embodiments, the enhancer (e.g., the medium chain fatty acid or the salt of a medium chain fatty acid) is solid at room temperature. In some embodiments, the chain length is from 8 to 14 carbon atoms. In other embodiments, the enhancer is a sodium salt of a medium chain fatty acid. In some embodiments, the enhancer is selected from the group consisting of sodium caprylate, sodium caprate and sodium laurate. Exemplary enhancers are further described in U.S. Pat. Nos. 7,658,938 and 7,670,626 and U.S. Published Application Nos. 2003/0091623 and 2007/0238707, which are incorporated by reference in their entirety.

In some embodiments, the pharmaceutical composition of the invention comprises, consists essentially of, or consists of a therapeutically effective amount of a selective factor Xa inhibitor or a pharmaceutically acceptable salt thereof, an enhancer, wherein the enhancer is a medium chain fatty acid or a salt, ester, ether, or derivative of a medium chain fatty acid and has a carbon chain length of from about 8 to about 14 carbon atoms, and one or more auxiliary excipients. In other embodiments, the pharmaceutical composition of the invention comprises, consists essentially of, or consists of a therapeutically effective amount of a selective factor Xa inhibitor or a pharmaceutically acceptable salt thereof, an enhancer, wherein the enhancer is a medium chain fatty acid or a salt thereof and has a carbon chain length of from about 8 to about 14 carbon atoms, and one or more auxiliary excipients. In other embodiments, the pharmaceutical composition of the invention comprises, consists essentially of, or consists of a therapeutically effective amount of a selective factor Xa inhibitor or a pharmaceutically acceptable salt thereof, an enhancer, wherein the enhancer is a medium chain fatty acid salt and has a carbon chain length of from about 8 to about 14 carbon atoms, and one or more auxiliary excipients. In each of these embodiments, the factor Xa inhibitor can be fondaparinux and/or the enhancer can be sodium caprate.

In some embodiments, the enhancer is present in a ratio of from 1:100,000 to 10:1 (inhibitor:enhancer). In some embodiments, the dosage form is a tablet, a capsule, or a multiparticulate dosage form. In some embodiments, the dosage form is a controlled release dosage form. In some embodiments, the tablet further comprises a rate controlling polymer material. In some embodiments, the rate-controlling polymer is hydroxypropyl methylcellulose (HPMC). In some embodiments, the rate-controlling polymer is a polymer of acrylic or methacrylic acid or their respective esters or copolymers of acrylic or methacrylic acid and/or their respective esters.

In some embodiments, the selective factor Xa inhibitor and enhancer and at least one auxiliary excipient are compressed into tablet form prior to coating with a rate controlling polymer. In some embodiments, the selective factor Xa inhibitor and enhancer and at least one auxiliary excipient are compressed into tablet form prior to coating with a delayed release polymer. In some embodiments, the selective factor Xa inhibitor, the enhancer, the rate controlling polymer and at least one auxiliary excipient are compressed to form a controlled release matrix tablet. In some embodiments, the controlled release matrix tablet is coated with a rate-controlling polymer. In some embodiments, the controlled release matrix is coated with a delayed release polymer. In some embodiments, the selective factor Xa inhibitor, the enhancer and at least one auxiliary excipient are compressed into the form of a multilayer tablet prior to coating with a rate controlling-polymer. In some embodiments, the selective factor Xa inhibitor, the enhancer and at least one auxiliary excipient are compressed into the form of a multilayer tablet prior to coating with a delayed release polymer. Yet, in another embodiment, the selective factor Xa inhibitor and enhancer are dispersed in the rate-controlling polymer material and compressed into the form of a multilayer tablet. In some embodiments, the multilayer tablet is coated with a rate-controlling polymer. In some embodiments, the multilayer tablet is coated with a delayed release polymer.

In some embodiments, the selective factor Xa inhibitor, the enhancer, at least one auxiliary excipient, and the rate-controlling polymer material are combined into a multiparticulate form. In some embodiments, the multiparticulate form comprises discrete particles, pellets, minitablets, or combinations thereof. In some embodiments, the pharmaceutical composition of the present invention comprises a blend of two or more populations of particles, pellets or mini-tablets having different in vitro or in vivo release characteristics. In some embodiments, the multiparticulate is encapsulated in hard or soft gelatin capsules. In another embodiment, the capsule is coated with a rate-controlling polymer. In some embodiments, the capsule is coated with a delayed release polymer. In some embodiments, the multiparticulate is incorporated into a sachet.

In some embodiments, the discrete particles or pellets are compressed into tablet form. In some embodiments, the tablet form is coated with a rate controlling polymer material. Yet, in another embodiment, the tablet form is coated with a delayed release polymer. In some embodiments, the discrete particles or pellets are compressed into a multilayer tablet. In some embodiments, the multilayer tablet is coated with a rate controlling material. In some embodiments, the multilayer tablet is coated with a delayed release polymer.

In the case of any of the above-mentioned embodiments, a controlled release coating (e.g., an enteric coating) may be applied to the final dosage form (capsule, tablet, multilayer tablet etc.). The controlled release coating may typically comprise a rate controlling polymer material as defined above. The dissolution characteristics of such a coating material may be pH dependent or independent of pH.

The pharmaceutical compositions of the invention can comprise one or more auxiliary excipients, such as for example rate-controlling polymeric materials, diluents, lubricants, disintegrants, plasticizers, anti-tack agents, opacifying agents, glidants, pigments, flavorings, and such like. As will be appreciated by those skilled in the art, the exact choice of excipients and their relative amounts will depend to some extent on the final dosage form.

One excipient that can be included in the composition is one or more saccharides. Any suitable saccharide may be used in the composition of the present invention. As used herein, the "saccharides" used in the invention include sugar alcohols, monosaccharides, disaccharides, and oligosaccharides. Exemplary sugar alcohols include, but not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-oligosaccharides, and mannan-oligosaccharides. In some embodiments, the saccharide is sorbitol, mannitol, or xylitol. In some embodiments, the saccharide is sorbitol. In some embodiments, the saccharide is sucrose.

Any suitable amounts of saccharide may be added in the compositions of the present invention. In some embodiments of the present invention, the ratio of the enhancer and saccharide may be adjusted to achieve a desired dissolution rate and/or compressibility of the resulting pharmaceutical composition. In some embodiments, the ratio of the enhancer and saccharide is 2:1 to 20:1. According to some embodiments, the ratio of the enhancer and saccharide is about 4:1 to 6:1. In another embodiment, the ratio of the enhancer and saccharide is about 5:1.

Any suitable grade of saccharide may be used in the composition of the present invention. However, in some embodiments, the selection of the grade of saccharide may be dependent upon the particle size distribution (PSD) of a specific grade of saccharide. Further, in another embodiment, the specific grade of the saccharide may affect the characteristics of the resulting pharmaceutical composition such as dissolution rate and/or compressibility. In some embodiments, the selection of the grade of saccharide is dependent upon the PSD of other excipients and the therapeutically active ingredient. In some embodiments, the saccharide is Parteck SI 150 (Merck KGaA, Darmstadt, Germany), a directly compressible sorbitol. In other embodiments, the saccharide is Parteck S1400 (Merck KGaA, Darmstadt, Germany).

Suitable diluents include, for example, pharmaceutically acceptable inert fillers such as microcrystalline cellulose, lactose, dibasic calcium phosphate, saccharides, and/or mixtures of any of the foregoing. Examples of diluents include microcrystalline cellulose such as that sold under the Trademark Avicel (FMC Corp., Philadelphia, Pa.), for example, Avicel™ pH101, Avicel™ pH102 and Avicel™ pH112; lactose such as lactose monohydrate, lactose anhydrous and Pharmatose DCL21; dibasic calcium phosphate such as Emcompress; mannitol; starch; sorbitol; sucrose; glucose; and combinations and mixtures thereof.

Suitable lubricants, including agents that act on the flowability of the powder to be compressed are, for example, colloidal silicon dioxide such as Aerosil™ 200; talc; stearic acid; magnesium stearate; calcium stearate; and combinations and mixtures thereof.

Suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

The term "rate controlling polymer material" as used herein includes hydrophilic polymers, hydrophobic polymers and mixtures of hydrophilic and/or hydrophobic polymers that are capable of controlling or retarding the release of the peptide or protein from a solid oral dosage form of the present invention. Suitable rate controlling polymer materials include those selected from the group consisting of hydroxyalkyl cellulose such as hydroxypropyl cellulose and hydroxypropyl methyl cellulose; poly(ethylene)oxide; alkyl cellulose such as ethyl cellulose and methyl cellulose; carboxymethyl cellulose; hydrophilic cellulose derivatives; polyethylene glycol; polyvinylpyrrolidone; cellulose acetate; cellulose acetate butyrate; cellulose acetate phthalate; cellulose acetate trimellitate; polyvinyl acetate phthalate; hydroxypropylmethyl cellulose phthalate; hydroxypropylmethyl cellulose acetate succinate; polyvinyl acetaldiethylamino acetate; poly (alkylmethacrylate) and poly(vinyl acetate). Other suitable hydrophobic polymers include polymers and/or copolymers derived from acrylic or methacrylic acid and their respective esters, zein, waxes, shellac and hydrogenated vegetable oils. Particularly useful in the practice of the present invention are poly acrylic acid, poly acrylate, poly methacrylic acid and poly methacrylate polymers such as those sold under the Eudragit tradename (Rohm GmbH, Darmstadt, Germany) specifically Eudragit® L, Eudragit® S, Eudragit® RL, and Eudragit® RS coating materials and mixtures thereof. Some of these polymers can be used as delayed release polymers to control the site where the drug is released. They include poly methacrylate polymers such as those sold under the Eudragit tradename (Rohm GmbH, Darmstadt, Germany) specifically Eudragit® L, Eudragit® S, Eudragit® RL, and Eudragit® RS coating materials and mixtures thereof.

Another aspect of the present invention provides a method of treating or preventing a medical condition, comprising administering to a patient suffering from said condition, a therapeutically effective amount of a selective factor Xa inhibitor or a pharmaceutically acceptable salt thereof together with an enhancer, wherein the enhancer is a medium chain fatty acid or a salt, ester, ether, or derivative of a medium chain fatty acid and has a carbon chain length of from about 4 to about 20 carbon atoms. In some embodiments, the medical condition is a thromboembolic condition, e.g., thrombophlebitis, phlebothrombosis, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, pulmonary embolism, arterial thrombosis, stroke, myocardial infarction, hepatic artery thrombosis, arterial embolus, or any combination thereof.

Another aspect of the present invention provides use of the compositions of the invention for treatment of a medical condition, e.g., a thromboembolic condition. The invention also relates to compositions and pharmaceutical formulations as described herein for use in the treatment of a medical condition, e.g. a thromboembolic condition.

Another aspect of the present invention provides use of the compositions of the invention in the manufacture of a medicament for treatment of a medical condition, e.g., a thromboembolic condition.

Another aspect of the present invention provides a process for manufacturing a solid oral dosage form of a pharmaceutical composition comprising the steps of: a) blending a selective factor Xa inhibitor or a pharmaceutically acceptable salt thereof with an enhancer, and optionally auxiliary excipients to form a blend; wherein the enhancer is a medium chain fatty acid or a salt, ester, ether, or derivative of a medium chain fatty acid and has a carbon chain length of from about 4 to about 20 carbon atoms; and b) forming a solid oral dosage from the blend by i) directly compressing the blend to form the solid oral dosage form, or ii) granulating the blend to form a granulate for incorporation into the solid oral dosage form, or iii) spray drying the blend to form a multiparticulate for incorporation into the solid oral dosage form. In some embodiments, the selective factor Xa inhibitor and the enhancer are blended in a ratio of from 1:100000 to 10:1 (inhibitor:enhancer).

Another aspect of the present invention provides a pharmaceutical composition of a selective factor Xa inhibitor or a pharmaceutically acceptable salt thereof for oral administration, the composition comprising, consisting essentially of, or consisting of a stable, transparent drug delivery composition. The stable, transparent drug delivery composition comprises, consists essentially of, or consists of (a) from about 1 to about 80 weight percent of a pharmaceutically acceptable oil; (b) from about 3 to about 98 weight percent (e.g., from about 3 to about 96.5 weight percent) surfactants; (c) from about 2 to about 60 weight percent polyethylene glycol; (d) from about 0.5 to about 15 weight percent water; and (e) a selective factor Xa inhibitor or a pharmaceutically acceptable salt thereof; wherein the ratio of the polyethylene glycol to water is at least 2:1. In certain embodiments, the composition does not contain a mixture of cholesterol and phospholipid. In some embodiments, the pharmaceutical composition of a selective factor Xa inhibitor further comprises an enhancer, wherein the enhancer is a medium chain fatty acid or a salt, ester, ether, or derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The stable drug delivery composition is further described in U.S. Pat. No. 5,707,648, which is incorporated by reference in its entirety.

"Pharmaceutically acceptable oils" include oils accepted in the food or pharmaceutical industry, e.g., triesters of glycerol having from about 9 to 83, e.g., 21-60, e.g., 21-45 carbon atoms. The triglycerides are further defined as short chain triglycerides having 9-15 carbon atoms, medium chain triglycerides having 21-45 carbon atoms, and long chain triglycerides having above 45 carbon atoms. Medium chain triglycerides are preferred. Examples of glycerol triesters include natural, edible oils such as canola, corn, olive, sunflower and coconut oils, triacetin, the decanoic acid esters, and chemically-synthesized oils such as 1-oleyl-2,3-diacetyl glycerol. Commercially available triglyceride oils, both natural and chemically-synthesized, are available from Karlshanms Lipid Specialties, U.S.A. as the Captex® series, and from Huls America Inc. as the Miglyol series. Other suitable oils include diesters of propylene glycol having from about 7 to 55, e.g., 15-40 carbon atoms, e.g., propylene glycol esters of capric and caprylic acids, and mixtures thereof, having from 19 to 23 carbon atoms. The diesters of propylene glycols are further defined as short chain having from 7-11 carbon atoms, medium chain having from 15-31 carbon atoms, and long chain having above 31 carbon atoms. Preferred propylene glycol diesters are the medium chain oils. Diesters of propylene glycols include propylene glycol esters of capric acid, caprylic acid, and mixtures thereof such as Captex® 200, and Captex® 800 (Karlshamns Lipid Specialties, Columbus, Ohio) and other ester groups as described above for glycerol.

Surfactants (surface active agents) which may be employed in the compositions include both ionic agents, i.e., cationic, anionic or zwitterionic, and non-ionic agents, or mixtures thereof. Examples of cationic surfactants include cetyldimethylethylammonium bromide, cetylpyridinium chloride and other salts of these surfactants. Short chain monohydroxyl alcohols, such as $C_1$ to $C_6$ alcohols, are preferably not employed as surfactants in these systems due to toxicity factors, thus the compositions are substantially free of such short chain monohydroxyl alcohols. Various surfactants also have permeation enhancement properties.

Examples of anionic surfactants include $C_{8-32}$ fatty acids and salts thereof, e.g., $C_{8-12}$, e.g., $C_8$; cholic acid and derivatives thereof such as deoxycholate, and its salts, ursodeoxycholic acid, and taurocholic acid; $C_{8-56}$ diesters of tartaric acid; phospholipids such as phosphatidic acid and phosphatidyl serine; $C_{5-29}$ monoesters of lactic acid; $C_{8-20}$ sulfonates, including alkyl-, olefin-, and alkylaryl derivatives; tridecyl- and dodecylbenzene sulfonic acids; and $C_{5-33}$ sarcosine and betaine derivatives.

Zwitterionics include such phospholipids as lecithin, phosphatidylethanolamine, and sphingomyelins.

Among the non-ionic surfactants which may be employed are ethoxylated castor oil; $C_{5-29}$ mono-glycerides and ethoxylated derivatives thereof; $C_{15-60}$ diglycerides and polyoxyethylene derivatives thereof having 1 to 90 POE groups; $C_{10-40}$ esters (10-40 carbon atoms in the alcohol) of long chain fatty acids (fatty acids having 16 carbon atoms and above); $C_{10-40}$ alcohols; sterols such as cholesterol, ergosterol, and $C_{2-24}$ esters thereof; $C_{8-96}$ ethoxylated fatty esters; $C_{14-130}$ sucrose fatty esters; and $C_{20-130}$ sorbitol and sorbitan monoesters, diesters, and triesters, and polyoxyethylene (POE) derivatives thereof having 1 to 90 POE groups, e.g., polyoxyethylene sorbitan monooleate, sorbitol hexaoleate POE (50).

Low HLB surfactants include $C_9$ to $C_{13}$ monoglycerides, $C_{19}$ to $C_{25}$ diglycerides of mono and poly unsaturated fatty acids, $C_{15}$ to $C_{23}$ diglycerides, and $C_{35}$ to $C_{47}$ diglycerides of mono and poly unsaturated fatty acids. Preferred low HLB surfactants are those containing at least about 80 percent by weight, e.g., at least about 90 percent by weight, e.g., at least about 95 percent by weight, of a monoglyceride or diglyceride containing $C_6$, $C_7$, $C_8$, $C_9$, or $C_{10}$ fatty acid functionalities, or mixtures thereof; e.g., a $C_9$, $C_{11}$, or $C_{13}$ monoglyceride or mixtures thereof, e.g., a $C_{11}$ or $C_{13}$ monoglyceride or mixtures thereof. Commercial examples of these surfactants include Imwitor 308, manufactured by Huls America, Inc., having about 80-90% wt. $C_{11}$ monoglycerides; and Glycerol Monocaprylin, manufactured by Sigma Chemicals as 1-monooctanoyl-rac-glycerol having about 99% wt. $C_{11}$ monoglycerides, and Glycerol Monocaprate, manufactured as 1-monodecanoyl-rac-glycerol by Sigma Chemicals, having about 99% wt. $C_{13}$ monoglycerides. In certain embodiments, the low HLB surfactant, or mixture of low HLB surfactants, will be only the above recited monoglycerides having a purity of at least about 80 weight percent.

High HLB surfactants include the sorbitan surfactants, e.g., those having an HLB of from about 13 to about 17. Such surfactants include POE (20) sorbitan monooleate, monostearate, monopalmitate, and monolaurate sold commercially as Tween 80, 60, 40, and 20, respectively, by ICI Inc., and POE (4) sorbitan monolaurate sold commercially as Tween 21 by ICI. Other high HLB surfactants include ethoxylated castor oil surfactants, e.g., those having an HLB of from about 12 to about 20, such as Cremophor EL, RH-40, and RH-60 and the Pluronic F-series sold by BASF Inc. Potassium oleate is also preferred as a high HLB surfactant.

The low HLB surfactant may be present in the composition in an amount of from about 1 to about 40, e.g., from about 5 to about 30, e.g., from about 10 to about 30 weight percent, e.g., from 20 to 30 weight percent. The high HLB surfactant may be present in the composition in an amount of from about 2 to about 60, e.g., from about 5 to about 50, e.g., from about 10 to about 40 weight percent.

One aspect of the present invention describes a pharmaceutical composition of a selective factor Xa inhibitor or a pharmaceutically acceptable salt thereof for oral administration, the composition comprising, consisting essentially of, or consisting of an emulsion composition, wherein an internal phase of the emulsion composition contains a therapeutically effective amount of a selective factor Xa inhibitor or a pharmaceutically acceptable salt thereof; and the internal phase comprises or consists essentially of a polar, nonaqueous oxygen-containing, pharmaceutically acceptable liquid selected from the group consisting of $C_2$-$C_{30}$ polyhydric alcohols, poly(ethylene or propylene)glycols with 4-200 repeating units, $C_2$-$C_{30}$ ester derivatives thereof and $C_1$-$C_5$ ether derivatives thereof. Examples of such materials include glycerin, propylene glycol, polyethylene glycol 200, 400, 600, 1500, 4000 and 6000 with the number correlating approximately with the number of repeating units and ranging from 4 to 200, ethylene glycol dimethyl ether, tetraethylene glycol dimethyl ether, triacetin, medium chain ($C_6$-$C_{10}$) triglycerides such as tricaprylin (caprylic acid ester of glycerol, and propylene glycol $C_8$ diester (Captex 200). In certain embodiments the internal phase is a $C_2$-$C_{10}$ polyhydric alcohol, a polyethylene glycol with n=4-80, or the methyl or ethyl ethers thereof. The emulsion may also contain lecithin as an emulsifier or surfactant. Egg or soya lecithin is suitable. The continuous phase of the emulsion may be a lower alkyl ester of a $C_8$-$C_{22}$ fatty acid such as ethyl palmitate or a triglyceride. The alkyl may be $C_{1-5}$, e.g., $C_{1-3}$. In some embodiments, the pharmaceutical composition of a selective factor Xa inhibitor further comprises an enhancer, wherein the enhancer is a medium chain fatty acid or a salt, ester, ether, or derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The emulsion composition is further described in U.S. Pat. No. 5,110,606, which is incorporated by reference in its entirety.

Further aspects of the present invention relate to microemulsion compositions containing a selective factor Xa inhibitor. In certain embodiments the microemulsions are water-in-oil microemulsions. In some embodiments the selective factor Xa inhibitor is present in an internal dispersed aqueous phase. In one aspect, the composition is a water-in-oil microemulsion comprising an internally dispersed aqueous phase containing the selective factor Xa inhibitor; a pharmaceutically acceptable oil; and a surfactant component (which may comprise a mixture of surfactants) having a HLB value of 7-14. The pharmaceutically acceptable oil is as defined above, but in some aspects is selected from the group consisting of mono and di-esters of propylene glycol having from about 15 to about 40 carbon atoms, $C_{9-83}$ triglycerides, $C_{7-55}$ mono- or di-esters of propylene glycol, or mixtures thereof. The microemulsions may further comprise an enhancer, e.g., a medium chain fatty acid salt, an ester, an ether, or a derivative of a medium chain fatty acid and has a carbon chain length of from about 4 to about 20 carbon atoms.

Preferably the internal aqueous phase of the microemulsion comprises up to about 60 volume percent, e.g., up to about 20 volume percent of the microemulsion composition. In some embodiments the pharmaceutically acceptable oil component of the microemulsion comprises from about 5 to about 99 volume percent, e.g., from about 30 to about 99 volume percent or about 5 to about 90 volume percent of the microemulsion composition. In one embodiment the surfactant component of the microemulsion comprises from about 1 to about 70 volume percent of the microemulsion composition.

Another aspect of the present invention provides a pharmaceutical composition of a selective factor Xa inhibitor or a pharmaceutically acceptable salt thereof for oral administration which is a water-in-oil microemulsion composition, wherein the microemulsion composition converts to an oil-in-water emulsion by the addition of water and the microemulsion composition comprises, consists essentially of, or consists of (a) up to about 20 volume percent of an internal dispersed aqueous phase containing a therapeutically effective amount of a selective factor Xa inhibitor or a pharmaceutically acceptable salt thereof; (b) from about 30 to about 99 volume percent of a continuous oil phase comprising mono and di-esters of propylene glycol having from about 15 to about 40 carbon atoms; and (c) from about 1 to about 70 volume percent of a surfactant or mixture of surfactants, wherein the surfactant or surfactant mixture has a HLB value of from 7 to 14. In some embodiments, the pharmaceutical composition of a selective factor Xa inhibitor further comprises an enhancer, wherein the enhancer is a medium chain fatty acid salt, an ester, an ether, or a derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The microemulsion composition is further described in U.S. Pat. No. 5,444,041, which is incorporated by reference in its entirety.

One aspect of the present invention describes a pharmaceutical composition of a selective factor Xa inhibitor or a pharmaceutically acceptable salt thereof for oral administration which is a water-in-oil microemulsion composition, wherein the microemulsion composition converts to an oil-in-water emulsion by the addition of water and the microemulsion composition comprises, consists essentially of, or consists of (a) up to about 60 volume percent, based upon the total volume of the microemulsion, of an internally dispersed aqueous phase containing a therapeutically effective amount of a selective factor Xa inhibitor or a pharmaceutically acceptable salt thereof; (b) from about 5 to about 90 volume percent of a continuous oil phase comprising at least one pharmaceutically acceptable oil; and (3) from about 1 to about 70 volume percent of a surfactant or mixture of surfactants, wherein the surfactant or surfactant mixture has a HLB value of from 7 to 14. In some embodiments, the pharmaceutical composition of a selective factor Xa inhibitor further comprises an enhancer, wherein the enhancer is a medium chain fatty acid salt, an ester, an ether, or a derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The microemulsion composition is further described in U.S. Pat. No. 5,646,109, which is incorporated by reference in its entirety.

Another aspect of the present invention provides a pharmaceutical composition of a selective factor Xa inhibitor or a pharmaceutically acceptable salt thereof for oral administration which is a water-in-oil microemulsion composition, wherein the microemulsion composition comprises, consists essentially of, or consists of (a) from about 5 to about 99 volume percent of an oil phase comprising at least one pharmaceutically acceptable oil; (b) up to about 60 volume percent of an aqueous phase comprising water; (c) a therapeutically effective amount of a selective factor Xa inhibitor or a pharmaceutically acceptable salt thereof; (d) from about 1 to about 70 volume percent of a mixture of surfactants having a combined HLB value of from about 7 to about 14 comprising (i) a low HLB surfactant having an HLB below 8, said low HLB surfactant being at least 40 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surfactant having a HLB value above about 8. In some embodiments, the pharmaceutical composition of a selective factor Xa inhibitor further comprises an enhancer, wherein the enhancer is a medium chain fatty acid salt, an ester, an ether, or a derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The microemulsion composition is further described in U.S. Pat. No. 5,688,761, which is incorporated by reference in its entirety.

One aspect of the present invention provides a pharmaceutical composition of a selective factor Xa inhibitor or a pharmaceutically acceptable salt thereof for oral administration which is a water-in-oil microemulsion composition, wherein the microemulsion composition comprises, consists essentially of, or consists of (a) up to about 60 volume percent of an internal dispersed aqueous phase containing a therapeutically effective amount of a selective factor Xa inhibitor or a pharmaceutically acceptable salt thereof; (b) from about 5 to about 99 volume percent of a continuous oil phase comprising at least one pharmaceutically acceptable oil comprising a $C_{9-83}$ triglyceride, a $C_{7-55}$ mono- and di-ester of propylene glycol, or mixtures thereof; and (c) from about 1 to about 70 volume percent of a surfactant or surfactant mixture comprising a $C_8$ fatty acid salt, wherein the surfactant or surfactant mixture has a HLB value of at least 7. In some embodiments, the pharmaceutical composition of a selective factor Xa inhibitor further comprises an enhancer, wherein the enhancer is a medium chain fatty acid salt, an ester, an ether, or a derivative of a medium chain fatty acid and has a carbon chain length of from about 4 to about 20 carbon atoms. In some embodiments, the pharmaceutical composition described above can provide a stable and reproducible bioavailability of the selective factor Xa inhibitor. The microemulsion composition is further described in U.S. Pat. No. 5,633,226, which is incorporated by reference in its entirety.

In some embodiments, the pharmaceutical composition described above can provide a reproducible and predictable bioavailability, $C_{max}$, or other pharmacokinetic characteristic of the selective factor Xa inhibitor.

In some embodiments, in the pharmaceutical compositions described above, the selective factor Xa inhibitor is fondaparinux or a pharmaceutically acceptable salt thereof.

Another aspect of the present invention provides a method for obtaining a reproducible pharmacokinetic characteristic (e.g., bioavailability, $C_{max}$, AUC, etc.) of a selective factor Xa inhibitor in a subject after oral administration, comprising orally administering a pharmaceutical composition of the present invention to said subject. In certain embodiments, the composition comprises, consists essentially of, or consists of (a) a therapeutically effective amount of a selective factor Xa inhibitor or a pharmaceutically acceptable salt thereof and (b) an enhancer, wherein the enhancer is a medium chain fatty acid or a salt, ester, ether, or derivative of a medium chain fatty acid and has a carbon chain length of from about 4 to about 20 carbon atoms.

In some embodiments, the pharmaceutical composition comprises, consists essentially of, or consists of: (a) from about 1 to about 80 weight percent of a pharmaceutically acceptable oil; (b) from about 3 to about 98 weight percent (e.g., from about 3 to about 96.5 weight percent) surface active agents; (c) from about 2 to about 60 weight percent polyethylene glycol; and (d) from about 0.5 to about 15 weight percent water; wherein the ratio of the polyethylene glycol to water is at least 2:1.

In some embodiments, the pharmaceutical composition is in a form of a transparent drug delivery composition, wherein the drug delivery composition comprises, consists essentially of, or consists of: (a) from about 1 to about 80 weight percent of a pharmaceutically acceptable oil; (b) from about 3 to about 98 weight percent (e.g., from about 3 to about 96.5 weight percent) surface active agents; (c) from about 2 to about 60 weight percent polyethylene glycol; and (d) from about 0.5 to about 15 weight percent water; wherein the ratio of the polyethylene glycol to water is at least 2:1.

In some embodiments, the pharmaceutical composition is an emulsion composition, wherein an internal phase of the emulsion composition contains a therapeutically effective amount of a selective factor Xa inhibitor or a pharmaceutically acceptable salt thereof; and the internal phase comprises or consists essentially of a polar, nonaqueous oxygen-containing, pharmaceutically acceptable liquid selected from the group consisting of $C_2$-$C_{30}$ polyhydric alcohols, poly(ethylene or propylene) glycols with 4-200 repeating units, $C_2$-$C_{30}$ ester derivatives thereof, and $C_1$-$C_5$ ether derivatives thereof.

In some embodiments, the pharmaceutical composition is a water-in-oil microemulsion composition, wherein the microemulsion composition converts to an oil-in-water emulsion by the addition of water and the microemulsion composition comprises, consists essentially of, or consists of (a) up to about 20 volume percent of an internal dispersed aqueous phase containing a therapeutically effective amount of selective factor Xa inhibitor or a pharmaceutically acceptable salt thereof, (b) from about 30 to about 99 volume percent of a continuous oil phase comprising mono and di-esters of propylene glycol having from about 15 to about 40 carbon atoms, and (c) from about 1 to about 70 volume percent of a surfactant or mixture of surfactants, wherein the surfactant or surfactant mixture has a HLB value of from 7 to 14.

In some embodiments, the pharmaceutical composition is a water-in-oil microemulsion composition, wherein the microemulsion composition converts to an oil-in-water emulsion by the addition of water and the microemulsion composition comprises, consists essentially of, or consists of (a) up to about 60 volume percent, based upon the total volume of the microemulsion, of an internally dispersed aqueous phase containing a therapeutically effective amount of a selective factor Xa inhibitor or a pharmaceutically acceptable salt thereof; (b) from about 5 to about 90 volume percent of a continuous oil phase comprising at least one pharmaceutically acceptable oil; and (c) from about 1 to about 70 volume percent of a surfactant or mixture of surfactants, wherein the surfactant or surfactant mixture has a HLB value of from 7 to 14.

In some embodiments, the pharmaceutical composition is a water-in-oil microemulsion composition, wherein the microemulsion composition comprises, consists essentially of, or consists of (a) from about 5 to about 99 volume percent of an oil phase comprising at least one pharmaceutically acceptable oil; (b) up to about 60 volume percent of an aqueous phase comprising water; (c) a therapeutically effective amount of a selective factor Xa inhibitor or a pharmaceutically acceptable salt thereof; (d) from about 1 to about 70 volume percent of a mixture of surfactants having a combined HLB value of from about 7 to about 14 comprising (i) a low HLB surfactant having a HLB below 8, said low HLB surfactant being at least 40 percent by weight of a $C_9$ monoglyceride, $C_{10}$ monoglyceride, $C_{11}$ monoglyceride, $C_{12}$ monoglyceride, or $C_{13}$ monoglyceride, and (ii) at least one surfactant having a HLB value above about 8.

In some embodiments, the pharmaceutical composition is a water-in-oil microemulsion composition, wherein the microemulsion composition comprises, consists essentially of, or consists of (a) up to about 60 volume percent of an internal dispersed aqueous phase containing a therapeutically effective amount of a selective factor Xa inhibitor or a pharmaceutically acceptable salt thereof; (b) from about 5 to about 99 volume percent of a continuous oil phase comprising at least one pharmaceutically acceptable oil comprising a $C_{9-83}$ triglyceride, a $C_{7-55}$ mono- and di-ester of propylene glycol, or mixtures thereof; and (c) from about 1 to about 70 volume percent of a surfactant or surfactant mixture comprising a $C_8$ fatty acid salt, wherein the surfactant or surfactant mixture has a HLB value of at least 7.

One aspect of the present invention provides a method for obtaining a reproducible pharmacokinetic characteristic (e.g., bioavailability, $C_{max}$, AUC, etc.) of a selective factor Xa inhibitor in a subject after oral administration, comprising orally administering a pharmaceutical composition of the invention to said subject.

In some embodiments of the invention, the pharmaceutical compositions of the invention provide a bioavailability of the selective factor Xa inhibitor or a pharmaceutically acceptable salt thereof of at least about 5% when orally administered to a human subject, e.g., at least about 5, 6, 7, 8, 9, 10, 11, 12, 13, 14, 15, 16, 17, 18, 19, 20, 21, 22, 23, 24, or 25% or more. In other embodiments of the invention, the pharmaceutical compositions of the invention provide a bioavailability of the selective factor Xa inhibitor or a pharmaceutically acceptable salt thereof of at least about 5% when intraduodenally administered to a beagle dog, e.g., at least about 5, 6, 7, 8, 9, 10, 11, 12, 13, 14, 15, 16, 17, 18, 19, 20, 21, 22, 23, 24, or 25% or more.

In some embodiments, the invention encompasses any pharmaceutical composition (e.g., compositions equivalent to the compositions described herein) that provides a bioavailability of the selective factor Xa inhibitor or a pharmaceutically acceptable salt thereof of at least about 5% when orally administered to a human subject, e.g., at least about 5, 6, 7, 8, 9, 10, 11, 12, 13, 14, 15, 16, 17, 18, 19, 20, 21, 22, 23, 24, or 25% or more. In other embodiments, the invention encompasses any pharmaceutical composition (e.g., compositions equivalent to the compositions described herein) that provides a bioavailability of the selective factor Xa inhibitor or a pharmaceutically acceptable salt thereof of at least about 5% when intraduodenally administered to a beagle dog, e.g., at least about 5, 6, 7, 8, 9, 10, 11, 12, 13, 14, 15, 16, 17, 18, 19, 20, 21, 22, 23, 24, or 25% or more.

In certain embodiments of the invention, the pharmaceutical compositions of the invention provide a reproducible bioavailability from subject to subject after oral administration, e.g., a decreased coefficient of variation (CV) relative to the CV of unenhanced compositions. In some embodiments, the CV for bioavailability is less than about 60%, e.g., less than about 60, 55, 50, 45, 40, 35, 30, 25, 20, 15% or less when orally administered to human subjects. In other embodiments, the CV for bioavailability is less than about 60%, e.g., less than about 60, 55, 50, 45, 40, 35, 30, 25, 20, 15% or less when intraduodenally administered to beagle dogs.

In certain embodiments of the invention, the pharmaceutical compositions of the invention provide a reproducible $C_{max}$ from subject to subject after oral administration, e.g., a decreased coefficient of variation (CV) relative to the CV of unenhanced compositions. In some embodiments, the CV for $C_{max}$ is less than about 70%, e.g., less than about 70, 65, 60, 55, 50, 45, 40, 35, 30, 25, 20, 15% or less when orally administered to human subjects. In other embodiments, the CV for C. is less than about 70%, e.g., less than about 70, 65, 60, 55, 50, 45, 40, 35, 30, 25, 20, 15% or less when intraduodenally administered to beagle dogs.

In certain embodiments of the invention, the pharmaceutical compositions of the invention provide a reproducible AUC from subject to subject after oral administration, e.g., a decreased coefficient of variation (CV) relative to the CV of unenhanced compositions. In some embodiments, the CV for AUC is less than about 60%, e.g., less than about 60, 55, 50, 45, 40, 35, 30, 25, 20, 15% or less when orally administered to human subjects. In other embodiments, the CV for AUC is less than about 60%, e.g., less than about 60, 55, 50, 45, 40, 35, 30, 25, 20, 15% or less when intraduodenally administered to beagle dogs.

In some embodiments of the invention, the dose of selective factor Xa inhibitor administered to a subject is a dose sufficient to treat or prevent a medical condition. For example, the total dose administered to a subject can be in the range of about 2 to about 200 mg or more, e.g., about 2, 4, 6, 8, 10, 15, 20, 25, 30, 35, 40, 45, 50, 55, 60, 65, 70, 75, 80, 85, 90, 95, 100, 120, 140, 160, 180, or 200 mg or more or any range therein. The dosage forms of the invention can comprise any convenient amount of selective factor Xa inhibitor, e.g., about 1, 2.5, 5, 7.5, 10, 15, 20, 25, 30, 35, 40, 45, 50, 55, 60, 70, 75, 80, 85, 90, 95, 100, 125, 150, 175, or 200 mg or more.

In some embodiments, in the methods described above, the selective factor Xa inhibitor is fondaparinux or a pharmaceutically acceptable salt thereof.

The present invention will now be described in more detail with reference to the following examples. However, these examples are given for the purpose of illustration and are not to be construed as limiting the scope of the invention.

In the examples, it can be seen that the formulations of the present invention can achieve a bioavailability increase for fondaparinux of over 9% as compared to subcutaneous injection and in certain formulations, over a 16% bioavailability increase in achieved, even up to a 18.5% bioavailability increase. It can also be seen that the formulations of the present invention significantly increased the bioavailability of the drug (fondaparinux) and decreased the variability of absorption compared to an unenhanced formulation. Comparable pharmacokinetic profiles were obtained with most preferred fondaparinux formulations to that shown with the subcutaneous reference injection. The greatest improvement in the examples is seen with the microemulsion formulations (GIPET™ II in the examples).

EXAMPLE 1

Bioavailability of Oral Dosage Forms of Fondaparinux

The aim of the study was to determine the feasibility of preparing an oral dosage form of fondaparinux using Gastrointestinal Permeation Enhancement Technology (GIPET™) penetration enhancing technology. An intraduodenally cannulated dog model was used to determine fondaparinux bioavailability from solutions of fondaparinux in GIPET™ matrices administered directly into the duodena of beagle dogs. GIPET™ I technology involves the use of enteric coated tablets while GIPET™ II technology is microemulsion based within an enteric coated soft gel/hard capsule shell. Two GIPET™ I formulations (high and low) and two GIPET™ II formulations (Form I and Form II) were prepared with the components listed in Tables 1 and 2. An unenhanced solution was administered as a control, and a subcutaneous (s.c.) injection was administered as a reference dosage form.

TABLE 1

| TI | Designation | Formulation | | Dosing | |
|---|---|---|---|---|---|
| | | Dose fondaparinux | Formulation | Volume | Flush |
| Test Item 1 | Reference subcutaneous | 1 mg | ARIXTRA® 2.5 mg/0.5 mL isotonic saline | 0.2 mL | — |
| Test Item 2 | Reference Unenhanced | 5 mg | In water | 10 mL | 3 mL |
| Test Item 3 | GIPET ™ I (High) | 5 mg | In solution containing 550 mg C10 | 10 mL | 3 mL |
| Test Item 4 | GIPET ™ I (Low) | 5 mg | In solution containing 275 mg C10 | 10 mL | +3 mL |
| Test Item 5 | GIPET ™ II Form I | 5 mg | In Capmul® MCM based microemulsion | 1 mL | 12 mL |

TABLE 1-continued

| TI | Designation | Dose fondaparinux | Formulation | Volume | Flush |
|---|---|---|---|---|---|
| Test Item 6 | GIPET ™ II Form II | 5 mg | In Capmul ® MCM C10 based microemulsion | 1 mL | 12 mL |

TABLE 2

| Raw Material | Capmul MCM Based % | Capmul MCM C10 Based % |
|---|---|---|
| Captex ® 300 (Glyceryl tricaprylate caprate) | 5.0 | 13.3 |
| Capmul ® MCM (Glyceryl caprylate caprate) | 41.9 | — |
| Capmul ® MCM C10 (Glyceryl caprate) | — | 36.6 |
| Tween ® 80 (Polyethylene oxide sorbitan mono-oleate) | 21.3 | 21.3 |
| PEG 400 | 23.3 | 23.3 |
| Purified water | 8.0 | 5.0 |
| fondaparinux | 0.5 | 0.5 |

Five female beagle dogs had previously been surgically implanted with duodenal access ports (DAPs). Each DAP is connected to a cannula which is inserted into the duodenum. Blood samples were taken at appropriate intervals after administration of each test item and assayed for anti-Factor Xa activity.

The study consisted of six (6) test items: a reference dose of commercially available fondaparinux (subcutaneous injection), an unenhanced aqueous formulation, and four (4) GIPET™ liquid formulations. The test items were administered weekly as single bolus doses. Test item details are given in Table 1.

Figure 2:
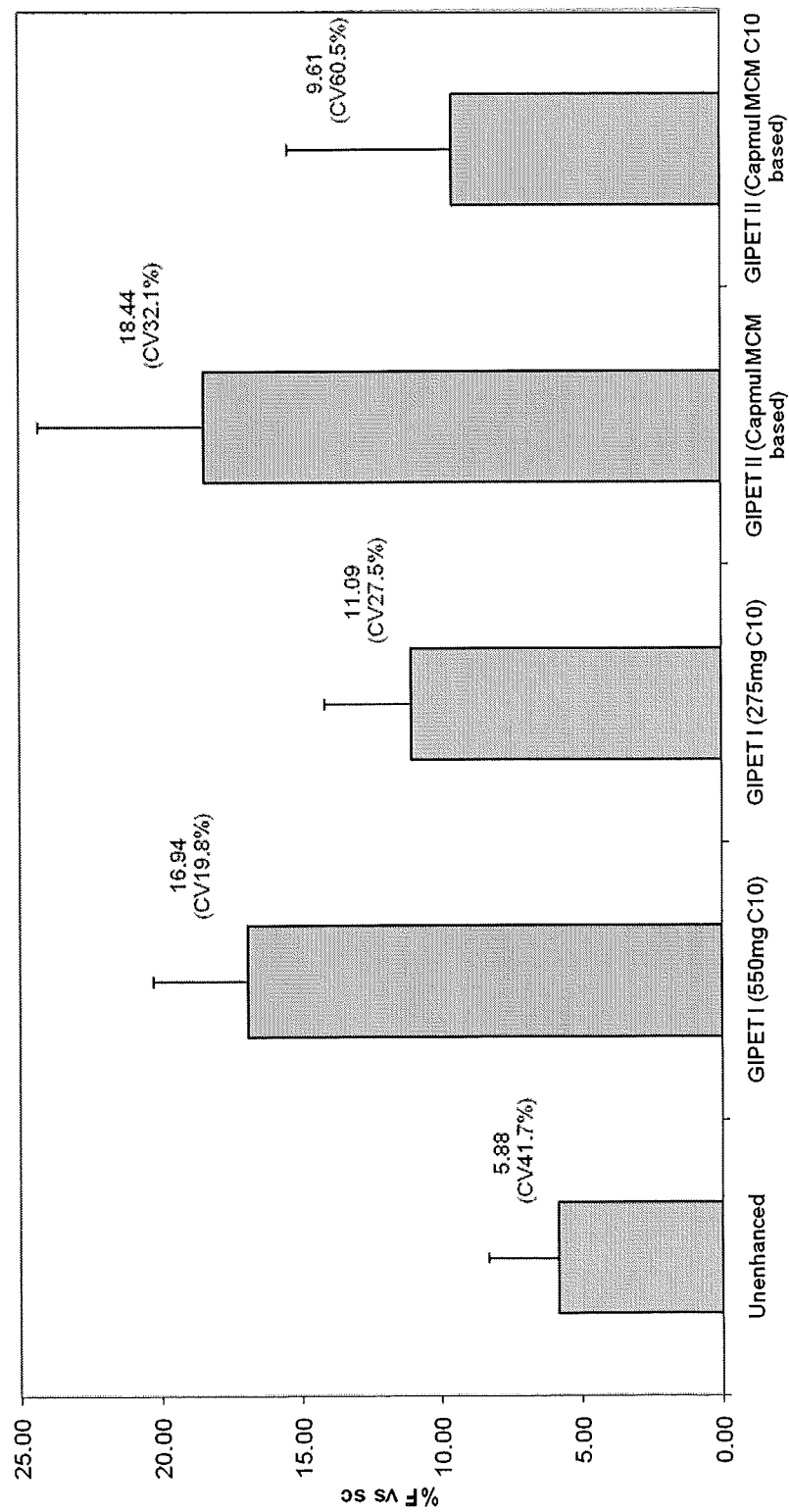
FIG. 2 shows the bioavailability of different GIPET™ formulations of fondaparinux in dogs following intraduodenal administration.

The pharmacokinetic results summary is shown in Table 3 and the raw data is shown in Tables 4-15. Plasma concentration levels are shown in FIG. 1. The 1 mg subcutaneous injection of fondaparinux had a $t^{1/2}$ of 7.3 h (CV 38.5%) and $C_{max}$ of 1.9 IU/mL. Bioavailability levels and CV are shown in FIG. 2. The bioavailability ($F_{rel}$ vs. sc) of the unenhanced fondaparinux solution administered to dogs by intra-duodenal instillation was 5.8% (CV 41.7%), with a $t^{1/2}$ of 8.1 h (CV 33.2%) and $C_{max}$ of 0.6 IU/mL.

Bioavailabilities over 16% of fondaparinux were achieved when administered in either a GIPET™ I or GIPET™ II formulation (Table 3). The bioavailability varied, depending on the formulation type (GIPET™ I or GIPET™ II) and the amount of GIPET I enhancer dosed. Administration of fondaparinux in a GIPET™ I matrix increased the bioavailability up to 16.9% (GIPET I High), while also lowering the variability of absorption (CV 19.8%, GIPET I High). A greater concentration of GIPET™ I enhancer resulted in an increase in absorption of the active. There was a decrease in the variability between animals by increasing the dose of GIPET™ I. Comparison of the $C_{max}$ showed that variability of the $C_{max}$ in the GIPET I High formulation (CV 9.0%) was approximately equivalent to the s.c. injection (CV 6.8%).

There was also a significant increase in bioavailability of fondaparinux on administration with GIPET™ II versus the unenhanced formulation (Table 3). Administration of fondaparinux in a GIPET™ II matrix increased the bioavailability up to 18.5% (GIPET™ II Form I) while also lowering the variability of absorption (CV 32.0%, GIPET™ II Form I). The estimates of $t^{1/2}$ were similar after administration of all treatments compared to the subcutaneous injection.

Conclusions from the study are that administration of fondaparinux in a GIPET™ I and/or GIPET™ II formulation significantly increased the bioavailability of the drug and decreased the variability of absorption compared to an unenhanced formulation. Comparable pharmacokinetic profiles were obtained with lead 5 mg fondaparinux/GIPET™ formulations to that shown with the subcutaneous reference injection (1 mg fondaparinux).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

TABLE 3

GIPET ™/fondaparinux mean pharmacokinetic parameters (mean ± SD, CV %)

| PK Parameters | 1 mg fondaparinux s.c. | 5 mg fondaparinux unenhanced | 5 mg fondaparinux + GIPET ™ I (High) | 5 mg fondaparinux + GIPET ™ I (Low) | 5 mg fondaparinux + GIPET ™ II (form I) | 5 mg fondaparinux + GIPET ™ II (form II) |
|---|---|---|---|---|---|---|
| Test Item | 1 | 2 | 3 | 4 | 5 | 6 |
| AUC (ng/mL · h) | 14430.54 ± 887.57 | 4248.28 ± 1797.46 | 12124.57 ± 1929.77 | 7951.51 ± 1937.05 | 13170.18 ± 3830.28 | 6915.71 ± 4054.15 |
| CV % | 6.15 | 42.24 | 15.92 | 24.36 | 29.09 | 58.62 |
| $F_{rel}$ vs. s.c. (%) | — | 5.88 ± 2.45 | 16.94 ± 3.35 | 11.09 ± 3.05 | 18.48 ± 5.91 | 9.61 ± 5.82 |
| CV % | — | 41.68 | 19.77 | 27.50 | 32.00 | 60.51 |
| $F_{rel}$ vs. unenhanced (%) | — | — | 320.92 ± 118.67 | 211.29 ± 94.42 | 340.18 ± 138.93 | 194.09 ± 152.55 |
| CV % | — | — | 36.98 | 44.69 | 40.84 | 78.60 |
| $T^{1/2}$ (h) | 7.34 ± 2.83 | 8.12 ± 2.70 | 5.77 ± 1.26 | 5.68 ± 1.73 | 6.13 ± 1.30 | 5.33 ± 0.91 |

TABLE 3-continued

GIPET ™/fondaparinux mean pharmacokinetic parameters (mean ± SD, CV %)

| PK Parameters | 1 mg fondaparinux s.c. | 5 mg fondaparinux unenhanced | 5 mg fondaparinux + GIPET ™ I (High) | 5 mg fondaparinux + GIPET ™ I (Low) | 5 mg fondaparinux + GIPET ™ II (form I) | 5 mg fondaparinux + GIPET ™ II (form II) |
|---|---|---|---|---|---|---|
| CV % | 38.54 | 33.22 | 21.77 | 30.47 | 21.26 | 17.00 |
| $C_{max}$ (ng/mL) | 1654.31 ± 112.21 | 511.90 ± 163.49 | 1761.59 ± 159.17 | 1297.64 ± 260.87 | 1833.96 ± 498.06 | 1027.3 ± 675.93 |
| CV % | 6.78 | 31.94 | 9.04 | | 27.16 | 65.80 |

TABLE 4

Subcutaneous Reference Leg

SC LEG

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0 | 0.00 | 0.00 | 0.00 | 0.00 | 0.00 | 0.00 | 0.00 | |
| 0.5 | 1717.97 | 1491.24 | 1491.24 | 1164.21 | 1111.89 | 1395.31 | 253.11 | |
| 1 | 1561.00 | 1491.24 | 1438.91 | 1543.56 | 1635.13 | 1533.97 | 74.02 | |
| 1.5 | 1517.40 | 1478.15 | 1792.10 | 1635.13 | 1635.13 | 1611.58 | 122.85 | |
| 2 | 1334.26 | 1334.26 | 1451.99 | 1399.67 | 1595.88 | 1423.21 | 108.42 | |
| 3 | 1151.13 | 1308.10 | 1124.97 | 1447.63 | 1255.78 | 1257.52 | 129.99 | |
| 5 | 1138.05 | 1007.24 | 1063.92 | 1164.21 | 1186.01 | 1111.89 | 74.45 | |
| 8 | 767.42 | 710.74 | 797.94 | 693.29 | 784.86 | 750.85 | 46.29 | |
| 12 | 366.27 | 436.03 | 409.87 | 313.94 | 409.87 | 387.20 | 48.00 | |
| 16 | 248.54 | 235.46 | 270.34 | 331.39 | 200.58 | 257.26 | 48.55 | |
| 24 | 0.00 | 174.41 | 178.77 | 0.00 | 0.00 | 70.64 | 96.74 | |
| 36 | 0.00 | 0.00 | 0.00 | 0.00 | 0.00 | 0.00 | 0.00 | |
| AUC | 13612.98 | 15099.85 | 15639.44 | 13973.79 | 13826.63 | 14430.54 | 887.57 | 6.15 |
| t½ | 4.92 | 9.79 | 10.40 | 7.51 | 4.06 | 7.34 | 2.83 | 38.54 |
| Cmax | 1717.97 | 1491.24 | 1792.10 | 1635.13 | 1635.13 | 1654.31 | 112.21 | 6.78 |

TABLE 5

Subcutaneous Reference Leg Summary

| | AUC | t½ | Cmax |
|---|---|---|---|
| | 15.61 | 4.92 | 1.97 |
| | 17.32 | 9.79 | 1.71 |
| | 17.93 | 10.40 | 2.06 |
| | 16.02 | 7.51 | 1.88 |
| | 15.86 | 4.06 | 1.88 |
| MEAN | 16.55 | 7.34 | 1.90 |
| Std dev. | 1.02 | 2.83 | 0.13 |
| % RSD | 6.15 | 38.54 | 6.78 |

TABLE 6

Test Item 2 Unenhanced

LEG 2

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0.00 | 0.00 | 0.00 | 0.00 | 0.00 | 0.00 | 0.00 | 0.00 | |
| 0.50 | 218.02 | 370.63 | 318.30 | 353.19 | 763.06 | 404.64 | 208.90 | |
| 1.00 | 331.39 | 492.72 | 392.43 | 414.23 | 758.70 | 477.89 | 167.25 | |
| 1.50 | 340.11 | 575.56 | 409.87 | 444.75 | 697.65 | 493.59 | 142.58 | |
| 2.00 | 340.11 | 549.40 | 436.03 | 401.15 | 723.82 | 490.10 | 151.22 | |
| 3.00 | 305.22 | 470.92 | 374.99 | 366.27 | 636.61 | 430.80 | 129.44 | |
| 5.00 | 296.50 | 462.20 | 305.22 | 366.27 | 497.08 | 385.45 | 90.92 | |
| 8.00 | 196.22 | 270.34 | 283.42 | 200.58 | 348.83 | 259.88 | 63.53 | |
| 12.00 | 0.00 | 309.58 | 0.00 | 0.00 | 218.02 | 105.52 | 148.07 | |
| 16.00 | 0.00 | 209.30 | 0.00 | 0.00 | 0.00 | 41.86 | 93.60 | |
| 24.00 | 0.00 | 0.00 | 0.00 | 0.00 | 0.00 | 0.00 | 0.00 | |
| 36.00 | 0.00 | 0.00 | 0.00 | 0.00 | 0.00 | 0.00 | 0.00 | |
| AUC | 2585.68 | 6433.68 | 3204.85 | 3074.04 | 5943.14 | 4248.28 | 1794.46 | 42.24 |
| SC AUC | 13612.98 | 15099.85 | 15639.44 | 13973.79 | 13826.63 | 14430.54 | | |
| % Bio | 3.80 | 8.52 | 4.10 | 4.40 | 8.60 | 5.88 | 2.45 | 41.68 |

TABLE 6-continued

Test Item 2 Unenhanced

LEG 2

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| t½ | 7.51 | 11.77 | 9.97 | 5.47 | 5.89 | 8.12 | 2.70 | 33.22 |
| Cmax ng/ml | 340.11 | 575.56 | 436.03 | 444.75 | 763.06 | 511.90 | 163.49 | 31.94 |

TABLE 7

Test Item 2 Unenhanced Summary

|  | AUC | SC AUC | % F vs sc | t½ | Cmax |
|---|---|---|---|---|---|
|  | 2.96 | 15.61 | 3.80 | 7.51 | 0.39 |
|  | 7.38 | 17.32 | 8.52 | 11.77 | 0.66 |
|  | 3.68 | 17.93 | 4.10 | 9.97 | 0.50 |
|  | 3.53 | 16.02 | 4.40 | 5.47 | 0.51 |
|  | 6.82 | 15.86 | 8.60 | 5.89 | 0.88 |
| MEAN | 4.87 | 16.55 | 5.88 | 8.12 | 0.59 |
| Std dev. | 2.06 |  | 2.45 | 2.70 | 0.19 |
| % RSD | 42.27 |  | 41.68 | 33.22 | 31.94 |

TABLE 8

Test Item 3 GIPET I High

LEG 3

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0 | 0 | 0 | 0 | 0 | 0 | 0.00 | 0.00 |  |
| 0.5 | 1909.83 | 1765.94 | 1508.68 | 1739.78 | 1883.67 | 1761.58 | 159.17 |  |
| 1 | 1465.07 | 1347.34 | 1059.56 | 1517.40 | 1334.26 | 1344.73 | 177.29 |  |
| 1.5 | 1229.62 | 1295.02 | 1360.43 | 1543.56 | 1308.10 | 1347.34 | 119.17 |  |
| 2 | 1399.67 | 1260.14 | 797.94 | 1386.59 | 1177.29 | 1204.33 | 245.14 |  |
| 3 | 1225.26 | 1050.84 | 837.18 | 1033.40 | 1351.70 | 1099.68 | 196.83 |  |
| 5 | 898.23 | 898.23 | 688.93 | 1181.65 | 976.72 | 928.75 | 177.23 |  |
| 8 | 662.77 | 606.09 | 510.16 | 815.38 | 702.01 | 659.28 | 113.22 |  |
| 12 | 361.91 | 401.15 | 261.62 | 409.87 | 449.11 | 376.73 | 71.42 |  |
| 16 | 0.00 | 231.10 | 174.41 | 252.90 | 348.83 | 201.45 | 129.00 |  |
| 24 | 0.00 | 0.00 | 0.00 | 0.00 | 0.00 | 0.00 | 0.00 |  |
| 36 | 0.00 | 0.00 | 0.00 | 0.00 | 0.00 | 0.00 | 0.00 |  |
| AUC | 11202.80 | 12083.59 | 9419.42 | 13955.26 | 13961.80 | 12124.57 | 1929.77 | 15.92 |
| SC AUC | 13612.98 | 15099.85 | 15639.44 | 13973.79 | 13826.63 | 14430.54 | 887.57 | 6.15 |
| % Bio | 16.46 | 16.00 | 12.05 | 19.97 | 20.20 | 16.94 | 3.35 | 19.77 |
| t½ | 5.29 | 5.75 | 5.17 | 4.74 | 7.93 | 5.77 | 1.26 | 21.77 |
| Cmax | 1909.83 | 1765.94 | 1508.68 | 1739.78 | 1883.67 | 1761.58 | 159.17 | 9.04 |

TABLE 9

Test Item 3 GIPET I High Summary

|  | AUC | SC AUC | % F vs sc | t½ | Cmax | Unenhanced AUC | % Frel vs unenhanced |
|---|---|---|---|---|---|---|---|
|  | 12.85 | 15.61 | 16.46 | 5.29 | 2.19 | 2.96 | 433.99 |
|  | 13.86 | 17.32 | 16.00 | 5.75 | 2.03 | 7.38 | 187.82 |
|  | 10.80 | 17.93 | 12.04 | 5.17 | 1.73 | 3.68 | 293.88 |
|  | 16.00 | 16.02 | 19.98 | 4.74 | 2.00 | 3.53 | 453.97 |
|  | 16.01 | 15.86 | 20.20 | 7.93 | 2.16 | 6.82 | 234.92 |
| MEAN | 13.90 | 16.55 | 16.94 | 5.77 | 2.02 |  | 320.92 |
| Std dev. | 2.21 | 1.02 | 3.35 | 1.26 | 0.18 |  | 118.67 |
| % RSD | 15.92 | 6.15 | 19.79 | 21.77 | 9.04 |  | 36.98 |

TABLE 10

Test Item 4 GIPET I Low

LEG 4

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0 | 0.00 | 0.00 | 0.00 | 0.00 | 0.00 | 0.00 | 0.00 | |
| 0.5 | 1517.40 | 863.35 | 1308.10 | 1530.48 | 680.21 | 1179.91 | 388.31 | |
| 1 | 1312.46 | 889.51 | 1207.81 | 562.48 | 1177.29 | 1029.91 | 304.72 | |
| 1.5 | 1229.62 | 667.13 | 915.67 | 575.56 | 981.08 | 873.81 | 260.54 | |
| 2 | 1229.62 | 723.82 | 1068.28 | 575.56 | 1242.70 | 968.00 | 303.15 | |
| 3 | 1098.81 | 601.73 | 854.63 | 466.56 | 1133.69 | 831.08 | 295.50 | |
| 5 | 806.66 | 514.52 | 597.37 | 392.43 | 802.30 | 622.66 | 181.29 | |
| 8 | 514.52 | 388.07 | 405.51 | 279.06 | 601.73 | 437.78 | 123.97 | |
| 12 | 213.66 | 218.02 | 252.90 | 209.30 | 274.70 | 233.71 | 28.69 | |
| 16 | 0.00 | 174.41 | 0.00 | 0.00 | 170.05 | 68.89 | 94.35 | |
| 24 | 0.00 | 0.00 | 0.00 | 0.00 | 0.00 | 0.00 | 0.00 | |
| 36 | 0.00 | 0.00 | 0.00 | 0.00 | 0.00 | 0.00 | 0.00 | |
| AUC | 9272.26 | 7218.54 | 7723.25 | 5260.75 | 10282.77 | 7951.51 | 1937.05 | 24.36 |
| SC AUC | 13612.98 | 15099.85 | 15639.44 | 13973.79 | 13826.63 | | | |
| % Bio | 13.62 | 9.56 | 9.88 | 7.53 | 14.87 | 11.09 | 3.05 | 27.50 |
| t½ | 3.62 | 6.93 | 5.66 | 7.80 | 4.39 | 5.68 | 1.73 | 30.47 |
| Cmax | 1517.40 | 889.51 | 1308.10 | 1530.48 | 1242.70 | 1297.64 | 260.87 | 20.10 |

TABLE 11

Test Item 4 GIPET I Low Summary

| | AUC | SC AUC | % F vs sc | t½ | Cmax | Unenhanced AUC | % Frel vs unenhanced |
|---|---|---|---|---|---|---|---|
| | 10.63 | 15.61 | 13.62 | 3.62 | 1.74 | 2.96 | 359.21 |
| | 8.28 | 17.32 | 9.56 | 6.93 | 1.02 | 7.38 | 112.20 |
| | 8.86 | 17.93 | 9.88 | 5.66 | 1.50 | 3.68 | 240.99 |
| | 6.03 | 16.02 | 7.53 | 7.80 | 1.76 | 3.53 | 171.06 |
| | 11.79 | 15.86 | 14.87 | 4.39 | 1.43 | 6.82 | 173.02 |
| MEAN | 9.12 | | 11.09 | 5.68 | 1.49 | | 211.29 |
| Std dev. | 2.22 | | 3.05 | 1.73 | 0.30 | | 94.42 |
| % RSD | 24.37 | | 27.50 | 30.47 | 20.10 | | 44.69 |

TABLE 12

Test Item 5 GIPET II

LEG 5

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0 | 0.00 | 0.00 | 0.00 | 0.00 | 0.00 | 0.00 | 0.00 | |
| 0.5 | 2158.37 | 1792.10 | 994.16 | 2223.77 | 2001.40 | 1833.96 | 498.06 | |
| 1 | 1752.86 | 1700.53 | 837.18 | 2066.80 | 1792.10 | 1629.89 | 465.21 | |
| 1.5 | 1504.32 | 1543.56 | 906.95 | 1792.10 | 1517.40 | 1452.86 | 327.16 | |
| 2 | 1491.24 | 1229.62 | 872.07 | 1622.05 | 1556.64 | 1354.32 | 308.01 | |
| 3 | 1273.22 | 1247.06 | 758.70 | 1465.07 | 1399.67 | 1228.74 | 277.63 | |
| 5 | 946.19 | 1098.81 | 558.12 | 1103.17 | 1098.81 | 961.02 | 234.90 | |
| 8 | 758.70 | 715.10 | 414.23 | 854.63 | 780.50 | 704.63 | 170.01 | |
| 12 | 348.83 | 392.43 | 279.06 | 449.11 | 553.76 | 404.64 | 103.98 | |
| 16 | 0.00 | 313.94 | 0.00 | 261.62 | 279.06 | 170.93 | 157.17 | |
| 24 | 0.00 | 0.00 | 0.00 | 0.00 | 170.05 | 34.01 | 76.05 | |
| 36 | 0.00 | 0.00 | 0.00 | 0.00 | 0.00 | 0.00 | 0.00 | |
| AUC | 12152.26 | 14014.13 | 7122.61 | 15570.77 | 16991.15 | 13170.18 | 3830.28 | 29.08 |
| SC AUC | 13612.98 | 15099.85 | 15639.44 | 13973.79 | 13826.63 | | | |
| % Bio | 17.85 | 18.56 | 9.11 | 22.29 | 24.58 | 18.48 | 5.91 | 32.00 |
| t½ | 4.77 | 6.74 | 7.00 | 4.68 | 7.44 | 6.13 | 1.30 | 21.26 |
| Cmax ng/ml | 2158.37 | 1792.10 | 994.16 | 2223.77 | 2001.40 | 1833.96 | 498.06 | 27.16 |

TABLE 13

Test Item 5 GIPET II Summary

|  | AUC | SC AUC | % F vs sc | t½ | Cmax | Unenhanced AUC | % Frel vs unenhanced |
|---|---|---|---|---|---|---|---|
|  | 13.94 | 15.61 | 17.85 | 4.77 | 2.48 | 2.96 | 470.78 |
|  | 15.89 | 17.32 | 18.35 | 6.74 | 2.06 | 7.38 | 215.38 |
|  | 8.17 | 17.93 | 9.11 | 7.00 | 1.14 | 3.68 | 222.24 |
|  | 17.86 | 16.02 | 22.29 | 4.68 | 2.55 | 3.53 | 506.67 |
|  | 19.48 | 15.86 | 24.58 | 7.44 | 2.30 | 6.82 | 285.84 |
| MEAN | 15.07 |  | 18.44 | 6.13 | 2.10 |  | 340.18 |
| Std dev. | 4.38 |  | 5.92 | 1.30 | 0.57 |  | 138.93 |
| % RSD | 29.09 |  | 32.08 | 21.26 | 27.16 |  | 40.84 |

TABLE 14

Test Item 6 GIPET II

LEG 6

| Time hr | Dog no. 3818 ng/ml | Dog no. 2640 ng/ml | Dog no. 7465 ng/ml | Dog no. 9261 ng/ml | Dog no. 7107 ng/ml | Mean ng/ml | Std dev. | % RSD |
|---|---|---|---|---|---|---|---|---|
| 0 | 0.00 | 0.00 | 0.00 | 0.00 | 0.00 | 0.00 | 0.00 | |
| 0.5 | 431.67 | 579.93 | 1098.81 | 2001.40 | 876.43 | 997.65 | 617.91 | |
| 1 | 366.27 | 536.32 | 1090.08 | 2145.29 | 771.78 | 981.95 | 704.78 | |
| 1.5 | 436.03 | 497.08 | 972.36 | 1818.26 | 758.70 | 896.49 | 558.11 | |
| 2 | 436.03 | 340.11 | 928.75 | 1883.67 | 645.33 | 846.78 | 622.07 | |
| 3 | 405.51 | 427.31 | 841.55 | 1438.91 | 558.12 | 734.28 | 430.51 | |
| 5 | 361.91 | 388.07 | 614.81 | 1159.85 | 466.56 | 598.24 | 329.03 | |
| 8 | 235.46 | 313.94 | 488.36 | 732.54 | 331.39 | 420.34 | 197.17 | |
| 12 | 0.00 | 174.41 | 200.58 | 392.43 | 200.58 | 193.60 | 139.18 | |
| 16 | 0.00 | 0.00 | 0.00 | 0.00 | 0.00 | 0.00 | 0.00 | |
| 24 | 0.00 | 0.00 | 0.00 | 0.00 | 0.00 | 0.00 | 0.00 | |
| 36 | 0.00 | 0.00 | 0.00 | 0.00 | 0.00 | 0.00 | 0.00 | |
| AUC | 3281.15 | 4469.35 | 7588.08 | 13586.81 | 5653.18 | 6915.71 | 4054.15 | 58.62 |
| SC AUC | 13612.98 | 15099.85 | 15639.44 | 13973.79 | 13826.63 |  |  |  |
| % Bio | 4.82 | 5.92 | 9.70 | 19.45 | 8.18 | 9.61 | 5.82 | 60.51 |
| t½ | 6.22 | 5.97 | 4.24 | 4.48 | 5.73 | 5.33 | 0.91 | 17.00 |
| Cmax | 436.03 | 579.93 | 1098.81 | 2145.29 | 876.43 | 1027.30 | 675.93 | 65.80 |

TABLE 15

Test Item 6 GIPET II Summary

|  | AUC | SC AUC | % F vs sc | t½ | Cmax | Unenhanced AUC | % Frel vs unenhanced |
|---|---|---|---|---|---|---|---|
|  | 3.76 | 15.61 | 4.82 | 6.22 | 0.50 | 2.96 | 127.11 |
|  | 5.13 | 17.32 | 5.92 | 5.97 | 0.67 | 7.38 | 69.47 |
|  | 8.70 | 17.93 | 9.70 | 4.24 | 1.26 | 3.68 | 236.77 |
|  | 15.58 | 16.02 | 19.45 | 4.48 | 2.46 | 3.53 | 441.99 |
|  | 6.48 | 15.86 | 8.18 | 5.73 | 1.01 | 6.82 | 95.12 |
| MEAN | 7.93 |  | 9.61 | 5.33 | 1.18 |  | 194.09 |
| Std dev. | 4.65 |  | 5.82 | 0.91 | 0.78 |  | 152.55 |
| % RSD | 58.62 |  | 60.51 | 17.00 | 65.80 |  | 78.60 |

That which is claimed is:

1. A method for obtaining a reproducible bioavailability of fondaparinux or a pharmaceutically acceptable salt thereof in a subject after oral administration, comprising orally administering to said subject a pharmaceutical composition comprising a therapeutically effective amount of fondaparinux or a pharmaceutically acceptable salt thereof and an enhancer, wherein the enhancer is a medium chain fatty acid salt and has a carbon chain length of from about 8 to about 14 carbon atoms, and wherein the bioavailability of fondaparinux or a pharmaceutically acceptable salt thereof has a coefficient of variation of no more than about 60%.

2. The method of claim 1, wherein the enhancer is solid at room temperature.

3. The method of claim 1, wherein the enhancer is a sodium salt of a medium chain fatty acid.

4. The method of claim 1, wherein the enhancer is selected from the group consisting of sodium caprylate, sodium caprate, and sodium laurate.

5. The method of claim 1, wherein the pharmaceutical composition is in a solid oral dosage form.

6. The method of claim 5, wherein the dosage form is a tablet, a capsule or a multiparticulate dosage form.

7. The method of claim 5, wherein the dosage form is a controlled release dosage form.

8. The method of claim 6, wherein the tablet further comprises a rate controlling polymer material.

9. The method of claim 8, wherein the rate-controlling polymer is hydroxypropyl methylcellulose.

10. The method of claim 8, wherein the rate-controlling polymer is a polymer of acrylic or methacrylic acid or their respective esters or copolymers of acrylic or methacrylic acid or their respective esters.

11. The method of claim 5, wherein the fondaparinux or a pharmaceutically acceptable salt thereof and enhancer and at least one auxiliary excipient are compressed into tablet form prior to coating with a rate controlling polymer or delayed release polymer.

12. The method of claim 8, wherein the fondaparinux or a pharmaceutically acceptable salt thereof, the enhancer, the rate controlling polymer and at least one auxiliary excipient are compressed to form a controlled release matrix tablet.

13. The method of claim 12, wherein the controlled release matrix tablet is coated with a rate-controlling polymer or delayed release polymer.

14. The method of claim 5, wherein the fondaparinux or a pharmaceutically acceptable salt thereof, the enhancer and at least one auxiliary excipient are compressed into the form of a multilayer tablet prior to coating with a rate controlling-polymer or delayed release polymer.

15. The method of claim 8, wherein the fondaparinux or a pharmaceutically acceptable salt thereof and enhancer are dispersed in the rate-controlling polymer material and compressed into the form of a multilayer tablet.

16. The method of claim 15, wherein the multilayer tablet is coated with a rate-controlling polymer or delayed release polymer.

17. The method of claim 8, wherein the fondaparinux or a pharmaceutically acceptable salt thereof, the enhancer, at least one auxiliary excipient, and the rate-controlling polymer material are combined into a multiparticulate form.

18. The method of claim 17, wherein the multiparticulate form comprises discrete particles, pellets, minitablets, or combinations thereof.

19. The method of claim 17, wherein the multiparticulate is encapsulated in hard or soft gelatin capsules.

20. The method of claim 19, wherein the capsule is coated with a rate-controlling polymer or delayed release polymer.

21. The method of claim 18, wherein the discrete particles or pellets are compressed into tablet form.

22. The method of claim 21, wherein the tablet form is coated with a rate controlling polymer material or delayed release polymer.

23. The method of claim 18, wherein the discrete particles or pellets are compressed into a multilayer tablet.

24. The method of claim 23, wherein the multilayer tablet is coated with a rate controlling material or delayed release polymer.

25. The method of claim 1, wherein the pharmaceutical composition provides a bioavailability of the fondaparinux or a pharmaceutically acceptable salt thereof of at least about 10% when orally administered to a human subject.

26. The method of claim 1, wherein the pharmaceutical composition provides a bioavailability of the fondaparinux or a pharmaceutically acceptable salt thereof of at least about 15% when orally administered to a human subject.

27. The method of claim 1, wherein the bioavailability of the fondaparinux or a pharmaceutically acceptable salt thereof has a coefficient of variation of no more than about 30%.

\* \* \* \* \*

UNITED STATES PATENT AND TRADEMARK OFFICE
CERTIFICATE OF CORRECTION

PATENT NO.        : 9,089,484 B2                               Page 1 of 1
APPLICATION NO.   : 13/073202
DATED             : July 28, 2015
INVENTOR(S)       : Leonard et al.

It is certified that error appears in the above-identified patent and that said Letters Patent is hereby corrected as shown below:

In the Specification
Column 19 Line 45: Please correct "for C. is less than"
                           to read -- for $C_{max}$ is less than --

Signed and Sealed this
First Day of March, 2016

Michelle K. Lee
*Director of the United States Patent and Trademark Office*